(12) United States Patent
Eberle et al.

(10) Patent No.: US 8,288,421 B2
(45) Date of Patent: Oct. 16, 2012

(54) PHENYLAMINOPYRIDINES

(75) Inventors: Martin Eberle, Bottmingen (CH); Felix Bachmann, Basel (CH); Alessandro Strebel, Oberwil (CH); Subho Roy, West Bengal (IN); Goutam Saha, West Bengal (IN); Godhuli Nandi, West Bengal (IN)

(73) Assignee: Basilea Pharmaceutica AG, Basel (CH)

( * ) Notice: Subject to any disclaimer, the term of this patent is extended or adjusted under 35 U.S.C. 154(b) by 1005 days.

(21) Appl. No.: 11/662,047

(22) PCT Filed: Sep. 5, 2005

(86) PCT No.: PCT/EP2005/054371
§ 371 (c)(1),
(2), (4) Date: Jan. 11, 2008

(87) PCT Pub. No.: WO2006/027348
PCT Pub. Date: Mar. 16, 2006

(65) Prior Publication Data
US 2008/0221171 A1   Sep. 11, 2008

(30) Foreign Application Priority Data
Sep. 6, 2004 (EP) .................................. 04405552

(51) Int. Cl.
*A61K 31/44* (2006.01)
*A61P 43/00* (2006.01)
*C07D 213/04* (2006.01)
(52) U.S. Cl. .......................... 514/352; 546/304; 546/312
(58) Field of Classification Search .................. None
See application file for complete search history.

(56) References Cited

U.S. PATENT DOCUMENTS
2009/0196912 A1   8/2009   Eickhoff et al.

FOREIGN PATENT DOCUMENTS
| WO | WO 02/47690 A | 6/2002 |
| WO | WO 2004/087679 A | 10/2004 |
| WO | WO 2005/058876 A | 6/2005 |
| WO | WO 2006010637 A2 * | 2/2006 |

OTHER PUBLICATIONS
International Search Report dated Dec. 21, 2005.
Written Report dated Dec. 21, 2005.

* cited by examiner

*Primary Examiner* — Yong Chu

(57) ABSTRACT

The invention relates to novel substituted 3-phenylamino-5-(3-aminophenyl)pyridines and corresponding pyrazines of formula (I),

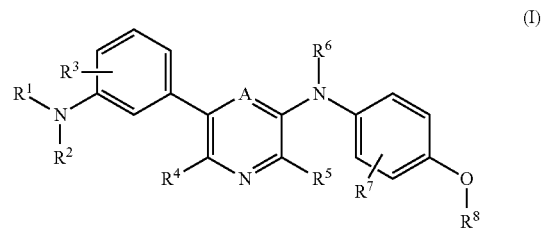

wherein A is CH or N, $R^1$ represents $C(=O)R^9$, $S(=O)_2R^{10}$, $P(=O)(OR^{11})_2$, optionally substituted phenyl or optionally substituted heteroaryl, and the other substituents have the meaning described in the specification, processes for the preparation thereof, pharmaceutical compositions containing same, the use thereof optionally in combination with one or more other pharmaceutically active compounds for the therapy of neoplastic diseases and autoimmune diseases, and a method for the treatment of such a diseases.

21 Claims, No Drawings

PHENYLAMINOPYRIDINES

CROSS-REFERENCE TO RELATED APPLICATION

This application is a National Stage Application of filed under 37 U.S.C. 371 PCT/EP2005/054371 filed Sep. 5, 2005, which claims priority from European Patent Application 04405552.3 filed on Sep. 6, 2004.

FIELD OF THE INVENTION

The invention relates to novel substituted 3-phenylamino-5-(3-aminophenyl)pyridines and corresponding pyrazines, processes for the preparation thereof, pharmaceutical compositions containing same, the use thereof optionally in combination with one or more other pharmaceutically active compounds for the therapy of neoplastic diseases and autoimmune diseases, and a method for the treatment of such a diseases.

BACKGROUND OF THE INVENTION

Cancer is one of the leading causes of death in humans. Although a variety of drugs against neoplastic diseases have been developed and techniques are available such as surgery and radiation therapy, there is still a need for alternative and improved methods of treatment of neoplastic diseases.

Autoimmune diseases are associated with abnormal lymphoproliferation as a result of defects in the termination of lymphocyte activation and growth. Often, such diseases are associated with inflammation like rheumatoid arthritis, insulin dependent diabetes mellitus, multiple sclerosis, systemic lupus erythematosus and the like. The treatment of such diseases is focused on anti-inflammatory and immunosuppressive drugs which in numerous cases show severe side effects. Hence, there is a need for alternative drugs with a new mode of action showing less side effects.

Apoptosis is a term used to describe a series of cellular events which occur to bring about programmed cell death. There are various apoptotic pathways, some of which have been characterized, whereas others remain to be elucidated. If the balance between cell division and apoptosis is disturbed, life-threatening diseases including cancer, autoimmune disorders, neurodegenerative and cardiovascular diseases may occur.

In recent years it has become evident that programmed cell death (apoptosis) is as important to the health of a multicellular organism as cell division. By repeated cell division and differentiation throughout development or tissue repair, surplus or even harmful cells are generated. In order to maintain tissue homeostasis these cells have to be removed or killed. The delicate interplay between cell growth and apoptosis in an organism is mirrored in the complex molecular balance that determines whether an individual cell undergoes division, arrests in the cell cycle or commits to programmed cell death.

Dysregulation of cell proliferation, or lack of appropriate cell death, has wide ranging clinical implications. A number of diseases associated with such dysregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like. Such cells may lose the normal regulatory control of cell division, and may also fail to undergo appropriate cell death.

As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or re-established in epithelial cells, in endothelial cells, in muscle cells, and in others which have lost contact with extracellular matrix. These cells are potentially able to colonize other organs and therefore can develop into pathologies like neoplasias, endometriosis and the like.

SUMMARY OF THE INVENTION

Substituted 3-phenylamino-5-(3-aminophenyl)-pyridines and corresponding 3-phenylamino-5-(3-aminophenyl)-pyridazines of formula (I) are selectively inducing apoptosis in cancer cells, and can be used for the treatment of neoplastic and autoimmune diseases. The invention relates to compounds of formula (I) for use as medicaments as defined hereinafter, to novel compounds of formula (I), to methods of synthesis of such compounds, to pharmaceutical compositions containing compounds of formula (I), to the use of a compounds of formula (I) for the preparation of a pharmaceutical composition for the treatment of neoplastic and autoimmune diseases, and to methods of treatment of neoplastic and autoimmune diseases using such compounds of formula (I) or of pharmaceutical compositions containing same.

DETAILED DESCRIPTION OF THE INVENTION

The invention relates to compounds of formula (I)

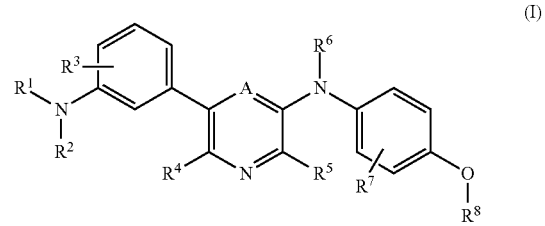

wherein A is CH or N;
$R^1$ represents $C(=O)R^9$, $S(=O)_2R^{10}$, $P(=O)(OR^{11})_2$, optionally substituted phenyl or optionally substituted heteroaryl;
$R^2$ represents hydrogen, lower alkylcarbonyl, amino-lower alkylcarbonyl, lower alkoxycarbonyl, aryl-lower alkylcarbonyl or arylmethoxycarbonyl;
$R^3$ represents hydrogen, lower alkyl, halo-lower alkyl, lower alkoxy-lower alkyl, halo-lower alkoxy-lower alkyl, cycloalkyl, optionally substituted alkenyl, optionally substituted alkinyl, optionally substituted heteroaryl, lower alkoxy, halo-lower alkoxy, lower alkoxy-lower alkoxy, alkenyloxy, aryloxy, heteroaryloxy, cyano, halogen or nitro;

$R^4$ and $R^5$, independently of each other, represent hydrogen, lower alkyl, halo-lower alkyl, lower alkoxy or halogen;

$R^6$ represents hydrogen, lower alkyl, lower alkylcarbonyl, lower alkoxycarbonyl or aryl-lower alkoxycarbonyl;

$R^7$ represents hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylamino, di-lower alkylamino, lower alkylcarbonylamino, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^8$ represents alkyl, cycloalkyl-lower alkyl, halo-lower alkyl, hydroxy-lower alkyl, lower alkoxy-lower alkyl, acyloxy-lower alkyl, lower alkoxy-lower alkoxy-lower alkyl, halo-lower alkoxy-lower alkyl, cyano-lower alkyl, carboxyalkyl, lower alkoxycarbonyl-lower alkyl; aminocarbonyl-lower alkyl wherein amino is unsubstituted or substituted by one or two substituents selected from lower alkyl, hydroxy-lower alkyl, alkoxy-lower alkyl and amino-lower alkyl, or wherein the two substituents on nitrogen form together with the nitrogen heterocyclyl; amino-lower alkyl, wherein amino is unsubstituted or substituted by one or two substitutents selected from lower alkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heterocyclyl and optionally substituted heteroaryl-lower alkyl, or wherein the two substituents on nitrogen form together with the nitrogen heterocyclyl; lower alkylsulfonyl, halo-lower alkylsulfonyl, lower alkoxy-lower alkylsulfonyl, arylsulfonyl, aryl-lower alkylsulfonyl, di-lower alkylphosphonyl, or di-phenylphosphonyl;

or $R^7$ and $R^8$ together with two carbon atoms of the phenyl ring and oxygen represent a 5, 6 or 7-membered ring optionally containing one or two further oxygen atoms and/or one nitrogen or sulfur atom, and optionally being substituted by oxo, lower alkyl or lower alkoxy.

$R^9$ represents lower alkyl, halo-lower alkyl, cycloalkyl-lower alkyl, hydroxy-lower alkyl, lower alkoxy-lower alkyl, aminoalkyl wherein amino is unsubstituted or substituted by one or two substituents selected from lower alkyl, hydroxy-lower alkyl, alkoxy-lower alkyl, amino-lower alkyl, lower alkylcarbonyl, lower alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, optionally substituted alkinyl, cycloalkyl, optionally substituted aryl, optionally substituted heteroaryl, arylalkyl, heteroarylalkyl, a group $-C(=O)-R^{12}$, a group $-C(=NOH)-R^{12}$ or a group $-C(=NO$-alkyl$)$-$R^{12}$;

$R^{10}$ represents lower alkyl, halo-lower alkyl, cycloalkyl-lower alkyl, lower alkoxy-lower alkyl, aminoalkyl wherein amino is unsubstituted or substituted by one or two substituents selected from lower alkyl, hydroxy-lower alkyl, alkoxy-lower alkyl, amino-lower alkyl, lower alkylcarbonyl, lower alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, cycloalkyl, optionally substituted aryl, optionally substituted heteroaryl, arylalkyl or heteroarylalkyl;

$R^{11}$ represents lower alkyl, halo-lower alkyl, lower alkoxy-lower alkyl, aryl or aryl-lower alkyl;

$R^{12}$ represents lower alkyl, optionally substituted aryl or optionally substituted heteroaryl;

and salts thereof;

with the proviso that, if A is CH, $R^1$ is C(=O)$R^9$ or S(=O)$_2$ $R^{10}$, $R^3$, $R^4$, $R^5$, $R^8$ and $R^7$ are all hydrogen, and $R^8$ is methyl, then $R^9$ or $R^{19}$ cannot be methyl.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Double bonds in principle can have E- or Z-configuration. The compounds of this invention may therefore exist as isomeric mixtures or single isomers. If not specified both isomeric forms are intended.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula (I).

Alkyl has from 1 to 12, preferably from 1 to 7 carbon atoms, and is linear or branched. Alkyl is preferably lower alkyl.

Lower alkyl has 1 to 7, preferably 1 to 4 carbon atoms and is butyl, such as n-butyl, sec-butyl, isobutyl, tert-butyl, propyl, such as n-propyl or isopropyl, ethyl or methyl. Preferably lower alkyl is methyl or ethyl. $C_2$-$C_7$-alkyl is lower alkyl with at least two carbon atoms, for example ethyl, propyl or butyl.

Cycloalkyl has preferably 3 to 7 ring carbon atoms, and may be unsubstitued or substituted, e.g. by lower alkyl or lower alkoxy. Cycloalkyl is, for example, cyclohexyl, cyclopentyl, methylcyclopentyl, or cyclopropyl.

Aryl stands for a mono- or bicyclic fused ring aromatic group with 5 to 10 carbon atoms, such as phenyl, 1-naphthyl or 2-naphthyl, or also a partially saturated bicyclic fused ring comprising a phenyl group, such as indanyl, dihydro- or tetrahydronaphthyl. Preferably, aryl is phenyl or naphthyl, in particular phenyl.

The term "optionally substituted aryl" stands for aryl substituted by up to four substituents independently selected from lower alkyl, halo-lower alkyl, cycloalkyl-lower alkyl, carboxy-lower alkyl, lower alkoxycarbonyl-lower alkyl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; hydroxy-lower alkyl, lower alkoxy-lower alkyl, aryloxy-lower alkyl, heteroaryloxy-lower alkyl, aryl-lower alkoxy-lower alkyl, heteroaryl-lower alkoxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, optionally substituted alkinyl, cycloalkyl, aryl, heteroaryl, heterocyclyl, hydroxy, lower alkoxy, halo-lower alkoxy, lower alkoxy-lower alkoxy, cycloalkyl-lower alkoxy, aryloxy, aryl-lower alkoxy, aryloxy-lower alkoxy, heteroaryloxy, heteroaryl-lower alkoxy, heteroaryloxy-lower alkoxy, optionally substituted alkenyloxy, optionally substituted alkinyloxy, cycloalkyloxy, heterocyclyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substitutents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl-lower alkyl, hydroxy-lower alkyl, lower alkoxy-lower alkyl, di-lower alkylamino-lower alkyl, cycloalkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, optionally substituted heteroarylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, and nitro; and wherein two substituents in ortho-position to each other can form a 5-, 6- or 7-membered carbocyclic or heterocyclic ring containing one, two or three oxygen atoms, one or two nitrogen atoms and/or one sulfur atom.

In particular, the substituents may be independently selected from lower alkyl, halo-lower alkyl, hydroxy-lower alkyl, lower alkoxy-lower alkyl, optionally substituted alkenyl, optionally substituted alkinyl, cyclohexyl, aryl, heteroaryl, heterocyclyl, hydroxy, lower alkoxy, halo-lower alkoxy, lower alkoxy-lower alkoxy, cycloalkyloxy; amino optionally substituted by one or two substituents selected from lower alkyl, cycloalkyl-lower alkyl, hydroxy-lower alkyl, lower alkoxy-lower alkyl, di-lower alkylamino-lower alkyl, cycloalkyl, optionally substituted heteroaryl, alkylcarbonyl, alkoxycarbonyl or aminocarbonyl, or wherein the two substituents on nitrogen form together with the nitrogen heterocyclyl; lower alkylcarbonyl, halo-lower alkylcarbonyl, carboxy, lower alkoxycarbonyl, lower alkoxy-lower alkoxycarbonyl; aminocarbonyl wherein amino is unsubstituted or substituted by one or two substitutents selected from lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, and nitro; and wherein two substituents in ortho-position to each other can form a 5- or 6-membered heterocyclic ring containing one or two oxygen atoms and/or one nitrogen atom.

In optionally substituted phenyl or aryl, substituents are preferably lower alkyl, halo-lower alkyl, lower alkoxy-lower alkyl, hydroxy, lower alkoxy, halo-lower alkoxy, lower alkoxy-lower alkoxy, methylenedioxy, halo, carboxy, cyano or nitro.

Heteroaryl represents an aromatic group containing at least one heteroatom selected from nitrogen, oxygen and sulfur, and is mono- or bicyclic. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include pyrrolyl, thienyl, furyl, pyrazolyl, imidazolyl, tchiazolyl, oxazolyl, isoxazolyl, oxadiazolyl, thiazolyl, isothiazolyl, thiadiazolyl, pyridyl, pyridazinyl, pyrimidinyl, pyrazinyl, and benzo fused derivatives of such monocyclic heteroaryl groups, such as indolyl, benzimidazolyl or benzofuryl, quinolinyl, isoquinolinyl, quinazolinyl, or purinyl. Preferably, heteroaryl is pyridyl, pyrimdinyl, pyrazinyl, pyridazinyl, thienyl, pyrazolyl, imidazolyl, thiazolyl, oxadiazolyl, triazolyl, oxazolyl, isoxazolyl, isothiazolyl or pyrrolyl, in particular pyridyl, pyrimidinyl, pyrazinyl, pyridazinyl, pyrazolyl, imidazolyl, thiazolyl, oxadiazolyl or triazolyl.

The term "optionally substituted heteroaryl" stands for heteroaryl substituted by up to three substituents independently selected from lower alkyl, halo-lower alkyl, cycloalkyl-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl, wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, amino-lower alkoxycarbonyl, lower alkoxy-lower alkoxycarbonyl and aminocarbonyl; optionally substituted alkenyl, optionally substituted alkinyl, cycloalkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; hydroxy, lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl-lower alkyl, hydroxy-lower alkyl, lower alkoxy-lower alkyl, di-lower alkylamino-lower alkyl, cycloalkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, and nitro.

In particular, the substituents on heteroaryl may be independently selected from lower alkyl, halo-lower alkyl, cycloalkyl-lower alkyl, lower alkoxy-lower alkyl, lower alkoxy-lower alkoxy-lower alkyl, optionally substituted alkenyl, optionally substituted alkinyl, cycloalkyl, aryl, heteroaryl, hydroxy, lower alkoxy, cycloalkyloxy, alkenyloxy, alkinyloxy, alkylmercapto, alkylsulfinyl, halo-lower alkylsulfinyl, alkylsulfonyl, arylsulfonyl; amino optionally substituted by one or two substitutents selected from lower alkyl, cycloalkyl-lower alkyl, hydroxy-lower alkyl, lower alkoxy-lower alkyl, di-lower alkylamino-lower alkyl, cycloalkyl, alkylcarbonyl, alkoxycarbonyl or aminocarbonyl, and wherein alkyl or lower alkyl in each case may be substituted by lower alkoxy or optionally substituted amino, or wherein the two substituents on nitrogen form together with the nitrogen heterocyclyl; lower alkylcarbonyl, halo-lower alkylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl-lower alkyl, hydroxy-lower alkyl, lower alkoxy-lower alkyl or cycloalkyl, or wherein the two substituents on nitrogen form together with the nitrogen heterocyclyl; cyano, halogen, and nitro.

In optionally substituted heteroaryl, substituents are preferably lower alkyl, halo-lower alkyl, lower alkoxy-lower alkyl, hydroxy, lower alkoxy, halo-lower alkoxy, lower alkoxy-lower alkoxy, methylenedioxy, halo, carboxy, cyano or nitro.

Alkenyl contains one or more, e.g. two or three, double bonds, and is preferably lower alkenyl, such as 1- or 2-butenyl, 1-propenyl, allyl or vinyl.

Alkinyl is preferably lower alkinyl, such as propargyl or acetylenyl.

In optionally substituted alkenyl or alkinyl, substituents are preferably lower alkyl, lower alkoxy, halo, optionally substituted aryl or optionally substituted heteroaryl, and are connected with a saturated or unsaturated carbon atom of alkenyl or alkinyl.

Heterocyclyl designates preferably a saturated, partially saturated or unsaturated, mono- or bicyclic ring containg 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl, tetrahydrofuranyl and tetrahydropyranyl.

Acyl designates, for example, alkylcarbonyl, cycloalkylcarbonyl, arylcarbonyl, aryl-lower alkylcarbonyl, or heteroarylcarbonyl. Lower acyl is preferably lower alkylcarbonyl, in particular propionyl or acetyl.

Hydroxyalkyl is especially hydroxy-lower alkyl, preferably hydroxymethyl, 2-hydroxyethyl or 2-hydroxy-2-propyl.

Cyanoalkyl designates preferably cyanomethyl and cyanoethyl.

Haloalkyl is preferably fluoroalkyl, especially trifluoromethyl, 3,3,3-trifluoroethyl or pentafluoroethyl.

Halogen is fluorine, chlorine, bromine, or iodine.

Lower alkoxy is especially methoxy, ethoxy, isopropyloxy, or tert-butyloxy.

Arylalkyl includes aryl and alkyl as defined hereinbefore, and is e.g. benzyl, 1-phenethyl or 2-phenethyl.

Heteroarylalkyl includes heteroaryl and alkyl as defined hereinbefore, and is e.g. 2-, 3- or 4-pyridylmethyl, 1- or 2-pyrrolylmethyl, 1-pyrazolylmethyl, 1-imidazolylmethyl, 2-(1-imidazolyl)ethyl or 3-(1-imidazolyl)propyl.

If $R^7$ and $R^8$ together with two carbon atoms of the phenyl ring and oxygen represent a 5, 6 or 7-membered ring, $R^7$ has to be in ortho position to the substituent $OR^8$. Such substituents $R^7/R^8$ are, for example, ethylene, 1-oxaethylene, 1-azaethylene, propylene, 1- or 2-oxapropylene, 1-oxapropylidene, 1- or 2-azapropylene, 1- or 2-azapropylidene, 1,2-diazapropylidene, butylene, 1-, 2- or 3-oxabutylene, 1,3-dioxabutylene, 1-, 2- or 3-azabutylene, or such groups carrying substituents oxo, lower alkyl (on carbon or on nitrogen) or lower alkoxy, whereby the numbering starts at the phenyl ring connection of $R^7$. Preferably $R^7$ and $R^8$ together with two carbon atoms of the phenyl ring and oxygen represent a 5 or 6-membered ring. Preferred substituents $R^7/R^8$ are ethylene, 1-oxaethylene, propylene, 1-oxapropylene, or such groups carrying substituents oxo, lower alkyl or lower alkoxy.

In substituted amino, the substituents are preferably those mentioned as substituents hereinbefore. In particular, substituted amino is alkylamino, dialkylamino, optionally substituted arylamino, optionally substituted arylalkylamino, lower alkylcarbonylamino, lower alkoxycarbonylamino or optionally substituted aminocarbonylamino.

Salts are especially the pharmaceutically acceptable salts of compounds of formula (I).

Such salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantane-carboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methyl-benzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compound of the formula (I) may be administered in the form of a pro-drug which is broken down in the human or animal body to give a compound of the formula (I). Examples of pro-drugs include in vivo hydrolysable esters and amides of a compound of the formula (I).

The compounds of formula (I) have valuable pharmacological properties. The invention also relates to compounds of formula (I) as defined hereinbefore for use as medicaments.

The efficacy of the compounds of the invention in inducing apoptosis in tumor cells can be demonstrated as follows:

Relative fluorescent activities of suitable tumor cell lines transfected with green fluorescent protein (GFP) are measured in the presence of compounds of the invention and of standard tumor drugs, using the method described in WO 99/35493. Suitable tumor cell lines are A20.2J, a BALB/c B cell lymphoma, PB-3c, an IL-3 dependent, non tumorigenic mastocyte line isolated from the bone marrow of a DBA/2 mouse, Jurkat, a human acute T cell leukemia cell line, K562, a human chronic myelogenous leukemia cell line, HL60, a human acute promyelocytic leukemia cell line, Ramos and Raji, human B-cell lymphoma cell lines, H9 and Hut78, human T-cell lymphoma cell lines, HeLa and KB, human squamous cell carcinoma cell lines, MCF7, SK-BR-3, PC3, HBL-100, SW480, H460 and H1792, human adenocarcinoma cell lines and HT-1080, a human fibrosarcoma cell line.

Preferred standard drugs as compounds for comparisons are: a) antimetabolites such as 5-fluorouracil (ICN), gemcitabine HCl (Gemzar™, Eli Lilly), b) alkylating agents such as oxaliplatin (Eloxantin™, Sanofi-Synthélabo), dacarbazin (Detimedac™, Medac), cyclo-phosphamide (Endoxan™, Asta) and carboplatin (Paraplatin™, Bristol-Meyers Squibb), c) cell-cycle inhibitor such as vinorelbine (Navelbine™, Robapharm), vinblastine (Velbe™, Eli Lilly), docetaxel (Taxotere™, Aventis), d) DNA breaker (topo-isomerase inhibitor, intercalator, strand breaker) such as doxorubicin HCl (Adriblastin™, Pharmacia-Upjohn), bleomycin (Asta-Medica), irinotecan (Campto™, Aventis), etoposide phosphate (Etopophos™, Bristol-Meyers Squibb), topotecan HCl, (Hycamtin™, GlaxoSmithKline), e) mixtures thereof, f) compounds interfering with the signal transduction pathway, such as caspase activity modifiers, agonists and antagonists of cell death receptors, modifiers of nucleases, phosphatases and kinases such as imatinib mesylate (Gleevec™, Novartis), dexamethasone, phorbol myristate acetate, cyclosporin A, quercetin, tamoxifen (Alexis Corporation, Switzerland).

Apoptosis is determined in a primary screen using a fluorescence plate reader and then in a secondary screen using FACS (fluorescence activated cell scanning). Compounds causing apoptosis without substantial cytotoxic side effects are chosen for further testing and characterization by using a combination of the following well established assays: A) Nuclear staining with Hoechst 33342 dye providing information about nuclear morphology and DNA fragmentation which are hallmarks of apoptosis. B) MTS proliferation assay measuring the metabolic activity of cells. Viable cells are metabolically active whereas cells with compromised respiratory chain show a reduced activity in this test. C) AnnexinV binding assay which reflects the phosphatidylserine content of the outer lipid bilayer of the plasma membrane. This event is considered an early hallmark of apoptosis. D) PI staining for cell cycle distribution which shows any alterations in the distribution among the different phases of the cell cycle. Cell cycle arresting points can be determined. E) Proliferation assay monitoring DNA synthesis by incorporating bromodeoxyuridine (BrdU). Inhibitory effects on growth/proliferation can be directly determined. F) Cystein proteinase dependency, respectively caspase dependency are determined by using specific inhibitors. This provides information about possible involvement of specific proteases in the mechanisms.

On the basis of these studies, a compound of formula (I) according to the invention shows therapeutic efficacy especially against neoplastic diseases and autoimmune diseases. In particular, the compounds of the invention are active against malignancies, e.g. epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuro-epitheliomatous neoplasms, meningiomas, nerve sheath tumors, granular cell tumors and alveolar soft part sarcomas, Hodgkin's and non Hodgkin's lymphomas, other lympho-reticular neoplasms, plasma cell tumors, mast cell tumors, immunoproliferative diseases, leukemias, miscellaneous myeloproliferative disorders, lymphoproliferative disorders and myelodysplastic syndromes.

The compounds of the invention are likewise active against autoimmune diseases, e.g. against systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barré syndrome, dermatomyositis/polymyositis, autoimmune hemolytic anemia, thrompocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia greata, primary biliary cirrhosis, autoimmune hepatitis, all forms of glomerulo-nephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory dieases with a possibility of autoimmune pathogensesis, such as pyoderma gangrensosum, lichen ruber, sarcoidosis (including Löfgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, Henoch-Schoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-VI (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e.g. stem cells).

A compound of formula (I) can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents. A compound of formula (I) can, besides or in addition, be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk. Particularly preferred is the use of compounds of formula (I) in combination with radiotherapy.

Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, an inhibitor of the interaction of an SH2 domain with a phosphorylated protein, an inhibitor of Bcl-2 and modulators of the Bcl-2 family members such as Bax, Bid, Bad, Bim, Nip3 and BH3-only proteins.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

With the groups of preferred compounds of formula (I) mentioned hereinafter, definitions of substituents from the general definitions mentioned hereinbefore may reasonably be used, for example, to replace more general definitions with more specific definitions or especially with definitions characterized as being preferred.

In particular, the invention refers to compounds of formula (I), wherein
A is CH or N;
$R^1$ represents $C(=O)R^9$, $S(=O)_2R^{10}$, $P(=O)(OR^{11})_2$, optionally substituted phenyl or optionally substituted heteroaryl;
$R^2$ represents hydrogen, lower alkylcarbonyl, amino-lower alkylcarbonyl or lower alkoxycarbonyl;
$R^3$ represents hydrogen, lower alkyl, halo-lower alkyl, lower alkoxy-lower alkyl, halo-lower alkoxy-lower alkyl, cycloalkyl, optionally substituted alkenyl, optionally substituted alkinyl, optionally substituted heteroaryl, lower alkoxy, halo-lower alkoxy, lower alkoxy-lower alkoxy, alkenyloxy, aryloxy, heteroaryloxy, cyano, halogen or nitro;
$R^4$ and $R^5$ represent hydrogen;
$R^6$ represents hydrogen, lower alkylcarbonyl or lower alkoxycarbonyl;
$R^7$ represents hydrogen, lower alkyl, halo-lower alkyl, optionally substituted alkenyl, optionally substituted alkinyl, optionally substituted heteroaryl, lower alkoxy, halo-lower alkoxy, lower alkoxy-lower alkoxy, alkenyloxy, alkylmercapto, alkylsulfinyl, halo-lower alkylsulfinyl, alkylsulfonyl, arylsulfonyl, heteroarylsulfonyl, lower alkylamino, di-lower alkylamino, lower alkylcarbonylamino, lower alkylcarbonyl, carboxy, lower alkoxycarbonyl, lower alkoxy-lower alkoxycarbonyl, cyano, halogen, or nitro;
$R^8$ represents alkyl, cycloalkyl-lower alkyl, halo-lower alkyl, hydroxy-lower alkyl, lower alkoxy-lower alkyl, acyloxy-lower alkyl, lower alkoxy-lower alkoxy-lower alkyl, halo-lower alkoxy-lower alkyl, cyano-lower alkyl, carboxyalkyl, lower alkoxycarbonyl-lower alkyl; aminocarbonyl-lower alkyl wherein amino is unsubstituted or substituted by one or two substituents selected from lower alkyl, hydroxy-lower alkyl, alkoxy-lower alkyl and amino-lower alkyl, or wherein the two substituents on nitrogen form together with the nitrogen heterocyclyl; amino-lower alkyl, wherein amino is unsubstituted or substituted by one or two substitutents selected from lower alkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heterocyclyl and optionally substituted heteroaryl-lower alkyl, or wherein the two substituents on nitrogen form together with the nitrogen heterocyclyl; lower alkylsulfonyl, halo-lower alkylsulfonyl, lower alkoxy-lower alkylsulfonyl, arylsulfonyl, aryl-lower alkylsulfonyl, di-lower alkylphosphonyl, or di-phenylphosphonyl;

or $R^7$ and $R^8$ together with two carbon atoms of the phenyl ring and oxygen represent a 5, 6 or 7-membered ring optionally containing one or two further oxygen atoms and/or one nitrogen or sulfur atom, and optionally being substituted by oxo, lower alkyl or lower alkoxy;

$R^9$ represents lower alkyl, halo-lower alkyl, cycloalkyl-lower alkyl, hydroxy-lower alkyl, lower alkoxy-lower alkyl, aminoalkyl wherein amino is unsubstituted or substituted by one or two substituents selected from lower alkyl, hydroxy-lower alkyl, alkoxy-lower alkyl, amino-lower alkyl, lower alkylcarbonyl, lower alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, optionally substituted alkinyl, cycloalkyl, optionally substituted aryl, optionally substituted heteroaryl, arylalkyl, heteroarylalkyl, or a group —C(=NO-alkyl)-$R^{12}$;

$R^{10}$ represents lower alkyl, halo-lower alkyl, cycloalkyl-lower alkyl, lower alkoxy-lower alkyl, aminoalkyl wherein amino is unsubstituted or substituted by one or two substituents selected from lower alkyl, hydroxy-lower alkyl, alkoxy-lower alkyl, amino-lower alkyl, lower alkylcarbonyl, lower alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, cycloalkyl, optionally substituted aryl, optionally substituted heteroaryl, arylalkyl or heteroarylalkyl;

$R^{11}$ represents lower alkyl, halo-lower alkyl, lower alkoxy-lower alkyl, aryl or aryl-lower alkyl;

$R^{12}$ represents lower alkyl, optionally substituted aryl or optionally substituted heteroaryl;

and salts thereof;

with the proviso that, if A is CH, $R^1$ is C(=O)$R^9$ or S(=O)$_2R^{10}$, $R^3$, $R^4$, $R^5$, $R^6$ and $R^7$ are all hydrogen, and $R^8$ is methyl, then $R^9$ or $R^{10}$ cannot be methyl.

More particularly, the invention refers to compounds of formula (I), wherein

A is CH or N;

$R^1$ represents C(=O)$R^9$, S(=O)$_2R^{10}$, P(=O)(O$R^{11}$)$_2$, optionally substituted phenyl or optionally substituted heteroaryl;

$R^2$ represents hydrogen;

$R^3$ represents hydrogen, lower alkyl, halo-lower alkyl, lower alkoxy-lower alkyl, halo-lower alkoxy-lower alkyl, cycloalkyl, lower alkoxy, halo-lower alkoxy, lower alkoxy-lower alkoxy, alkenyloxy, cyano, halogen or nitro;

$R^4$ and $R^5$ represent hydrogen;

$R^6$ represents hydrogen, lower alkylcarbonyl or lower alkoxycarbonyl;

$R^7$ represents hydrogen, lower alkyl, halo-lower alkyl, optionally substituted heteroaryl, lower alkoxy, halo-lower alkoxy, lower alkoxy-lower alkoxy, alkenyloxy, lower alkylamino, di-lower alkylamino, lower alkylcarbonylamino, lower alkylcarbonyl, carboxy, lower alkoxycarbonyl, lower alkoxy-lower alkoxycarbonyl, cyano, halogen, or nitro;

$R^8$ represents alkyl, cycloalkyl-lower alkyl, halo-lower alkyl, hydroxy-lower alkyl, lower alkoxy-lower alkyl, acyloxy-lower alkyl, lower alkoxy-lower alkoxy-lower alkyl, halo-lower alkoxy-lower alkyl, carboxyalkyl, lower alkoxycarbonyl-lower alkyl; aminocarbonyl-lower alkyl wherein amino is unsubstituted or substituted by one or two substituents selected from lower alkyl, hydroxy-lower alkyl, alkoxy-lower alkyl and amino-lower alkyl, or wherein the two substituents on nitrogen form together with the nitrogen heterocyclyl; amino-lower alkyl, wherein amino is unsubstituted or substituted by one or two substitutents selected from lower alkyl, cycloalkyl-lower alkyl, hydroxy-lower alkyl, lower alkoxy-lower alkyl, or wherein the two substituents on nitrogen form together with the nitrogen heterocyclyl; optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, lower alkoxycarbonyl, lower alkoxy-lower alkoxycarbonyl, lower alkylsulfonyl, lower alkoxy-lower alkylsulfonyl, di-lower alkylphosphonyl, or di-phenylphosphonyl;

$R^9$ represents lower alkyl, halo-lower alkyl, cycloalkyl-lower alkyl, hydroxy-lower alkyl, lower alkoxy-lower alkyl, aminoalkyl wherein amino is unsubstituted or substituted by one or two substituents selected from lower alkyl, hydroxy-lower alkyl, alkoxy-lower alkyl, amino-lower alkyl, lower alkylcarbonyl, lower alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, optionally substituted alkinyl, cycloalkyl, optionally substituted aryl, optionally substituted heteroaryl, arylalkyl, heteroarylalkyl, or a group —C(=NO-alkyl)-$R^{12}$;

$R^{10}$ represents lower alkyl, halo-lower alkyl, cycloalkyl-lower alkyl, lower alkoxy-lower alkyl, cycloalkyl, optionally substituted aryl, optionally substituted heteroaryl, arylalkyl or heteroarylalkyl;

$R^{11}$ represents lower alkyl, halo-lower alkyl, lower alkoxy-lower alkyl, aryl or aryl-lower alkyl;

$R^{12}$ represents lower alkyl, optionally substituted aryl or optionally substituted heteroaryl;

and salts thereof;

with the proviso that, if A is CH, $R^1$ is C(=O)$R^9$ or S(=O)$_2R^{10}$, $R^3$, $R^4$, $R^5$, $R^6$ and $R^7$ are all hydrogen, and $R^8$ is methyl, then $R^9$ or $R^{10}$ cannot be methyl.

Still more preferably, the invention relates to compounds of formula (I), wherein A is CH or N;

$R^1$ represents C(=O)$R^9$, S(=O)$_2R^{10}$, P(=O)(O$R^{11}$)$_2$, optionally substituted phenyl or optionally substituted heteroaryl;

$R^2$ represents hydrogen;

$R^3$ represents hydrogen, lower alkyl, halo-lower alkyl, lower alkoxy, cyano, halogen or nitro;

$R^4$ and $R^5$ represent hydrogen;

$R^6$ represents hydrogen;

$R^7$ represents hydrogen, lower alkyl, halo-lower alkyl, lower alkoxy, halo-lower alkoxy, lower alkoxy-lower alkoxy, alkenyloxy, lower alkylamino, di-lower alkylamino, lower alkylcarbonylamino, lower alkylcarbonyl, carboxy, lower alkoxycarbonyl, lower alkoxy-lower alkoxycarbonyl, cyano, halogen, or nitro;

$R^8$ represents alkyl, hydroxy-lower alkyl, lower alkoxy-lower alkyl, acyloxy-lower alkyl, lower alkoxy-lower alkoxy-lower alkyl, halo-lower alkoxy-lower alkyl, carboxyalkyl, lower alkoxycarbonyl-lower alkyl; amino-lower alkyl, wherein amino is unsubstituted or substituted by one or two substitutents selected from lower alkyl, cycloalkyl-lower alkyl, hydroxy-lower alkyl, lower alkoxy-lower alkyl, or wherein the two substituents on nitrogen form together with the nitrogen heterocyclyl; optionally substituted phenyl-lower alkyl, optionally substituted heteroaryl-lower alkyl, optionally substituted alkenyl, optionally substituted alkinyl, cycloalkyl, lower alkoxycarbonyl, lower alkoxy-lower alkoxycarbonyl, lower alkylsulfonyl, lower alkoxy-lower alkylsulfonyl, or di-lower alkylphosphonyl;

$R^9$ represents $C_2$-$C_7$-alkyl, halo-lower alkyl, cycloalkyl-lower alkyl, hydroxy-lower alkyl, lower alkoxy-lower alkyl, aminoalkyl wherein amino is unsubstituted or substituted by one or two substituents selected from lower alkyl, hydroxy-lower alkyl, alkoxy-lower alkyl, amino-lower alkyl, lower alkylcarbonyl, lower alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, optionally substituted alkinyl, cycloalkyl, optionally substituted aryl, optionally substituted heteroaryl, arylalkyl, heteroarylalkyl, or a group —C(=NO-alkyl)-$R^{12}$;

$R^{10}$ represents $C_2$-$C_7$-alkyl, lower alkoxy-lower alkyl, optionally substituted aryl, optionally substituted heteroaryl, arylalkyl or heteroarylalkyl;

$R^{11}$ represents lower alkyl, halo-lower alkyl, lower alkoxy-lower alkyl, aryl or aryl-lower alkyl;

$R^{12}$ represents lower alkyl, optionally substituted aryl or optionally substituted heteroaryl;

and salts thereof.

Even more preferably, the invention relates to compounds of formula (I), wherein A is CH or N;

$R^1$ represents C(=O)$R^9$ or optionally substituted heteroaryl;

$R^2$ represents hydrogen;

$R^3$ represents hydrogen, lower alkyl, halo-lower alkyl, lower alkoxy, cyano or halogen;

$R^4$ and $R^5$ represent hydrogen;

$R^6$ represents hydrogen;

$R^7$ represents hydrogen, lower alkyl, halo-lower alkyl, lower alkoxy, lower alkylcarbonylamino, lower alkylcarbonyl, carboxy, lower alkoxycarbonyl, lower alkoxy-lower alkoxycarbonyl, cyano or halogen;

$R^8$ represents alkyl, hydroxy-lower alkyl, lower alkoxy-lower alkyl, acyloxy-lower alkyl, lower alkoxy-lower alkoxy-lower alkyl, carboxyalkyl, lower alkoxycarbonyl-lower alkyl; amino-lower alkyl, wherein amino is unsubstituted or substituted by one or two substitutents selected from lower alkyl, cycloalkyl-lower alkyl, hydroxy-lower alkyl, lower alkoxy-lower alkyl, or wherein the two substituents on nitrogen form together with the nitrogen heterocyclyl; optionally substituted alkenyl, optionally substituted alkinyl, cycloalkyl, lower alkoxycarbonyl, lower alkoxy-lower alkoxycarbonyl, lower alkylsulfonyl, lower alkoxy-lower alkylsulfonyl, or di-lower alkylphosphonyl;

$R^9$ represents $C_2$-$C_7$-alkyl, halo-lower alkyl, cycloalkyl-lower alkyl, hydroxy-lower alkyl, lower alkoxy-lower alkyl, aminoalkyl wherein amino is unsubstituted or substituted by one or two substituents selected from lower alkyl, hydroxy-lower alkyl, alkoxy-lower alkyl, amino-lower alkyl, lower alkylcarbonyl, lower alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, optionally substituted alkinyl, cycloalkyl, optionally substituted aryl, optionally substituted heteroaryl, arylalkyl, heteroarylalkyl, or a group —C(=NO-alkyl)-$R^{12}$;

$R^{12}$ represents lower alkyl, optionally substituted aryl or optionally substituted heteroaryl;

and salts thereof.

Particularly preferred are compounds of formula (I), wherein

A is CH or N;

$R^1$ represents C(=O)$R^9$ or or S(=O)$_2$$R^{10}$;

$R^2$ represents hydrogen;

$R^3$ represents hydrogen or lower alkyl;

$R^4$ and $R^5$ represent hydrogen;

$R^6$ represents hydrogen;

$R^7$ represents hydrogen or lower alkoxy;

$R^8$ represents lower alkyl, benzyl or allyl;

$R^9$ represents $C_2$-$C_7$-alkyl, optionally substituted aryl or optionally substituted heteroaryl;

$R^{10}$ represents $C_2$-$C_7$-alkyl;

and salts thereof.

More particularly preferred are compounds of formula (I), wherein

A is CH;

$R^1$ represents C(=O)$R^9$ or S(=O)$_2$$R^{10}$;

$R^2$, $R^3$, $R^4$, $R^5$, $R^6$ and $R^7$ represent hydrogen;

$R^8$ represents lower alkyl;

$R^9$ represents $C_2$-$C_7$-alkyl, optionally substituted aryl or optionally substituted heteroaryl;

$R^{10}$ represents $C_2$-$C_7$-alkyl;

and salts thereof.

Most preferred are the compounds of the Examples 2 to 7 and 9 to 66, especially the compounds of Examples 2, 4, 11, 12, 13, 14, 16, 17, 18, 20, 21, 22, and 26.

Method of Preparation

A compound of the invention may be prepared by processes that, though not applied hitherto for the new compounds of the present invention, are known per se, in particular A) a process, wherein a compound of formula (II)

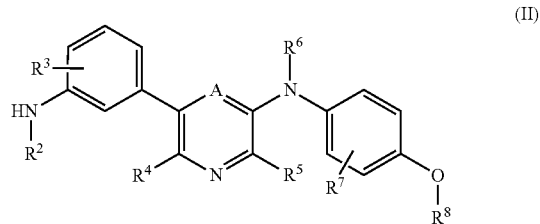

(II)

wherein A, $R^2$, $R^3$, $R^4$, $R^5$, $R^6$, $R^7$ and $R^8$ are as defined under formula (I) and is reacted with a compound of formula (III)

$R^1$—Z (IIIa)

wherein $R^1$ is C(=O)$R^9$, S(=O)$_2$$R^{10}$, or P(=O)(O$R^{11}$)$_2$ as defined under formula (I), and Z is hydroxy or halogen, optionally in the presence of a dehydrating agent; or B) a process, wherein a compound of formula (II)

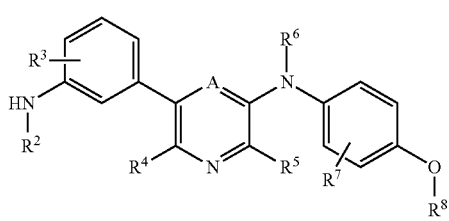

wherein A, R$^2$, R$^3$, R$^4$, R$^5$, R$^6$, R$^7$ and R$^8$ are as defined under formula (I) is reacted with a compound of formula (III)

wherein R$^1$ is optionally substituted phenyl or optionally substituted heteroaryl as defined under formula (I), and L is halogen or sulfonate, optionally in the presence of a catalyst, or C) a process, wherein a compound of formula (IV)

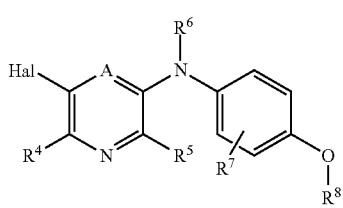

wherein A, R$^4$, R$^5$, R$^6$, R$^7$ and R$^8$ are as defined under formula (I) and Hal is halogen, is reacted with a compound of formula (V)

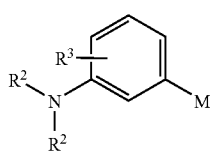

wherein R$^1$, R$^2$ and R$^3$ are as defined under formula (I) and M represents B(OH)$_2$ or an ester thereof, or Si(OR)$_3$, in the presence of a suitable catalyst;

and, if so desired, an obtainable compound of formula (I) is converted into another compound of formula (I), a free compound of formula (I) is converted into a salt, an obtainable salt of a compound of formula (I) is converted into the free compound or another salt, and/or a mixture of isomeric compounds of formula (I) is separated into the individual isomers.

In method A), the reaction may be performed in the presence of a suitable base if Z is halogen, e.g. with a metal carbonate or bicarbonate such as potassium carbonate or potassium hydrogen carbonate, or preferably with a tertiary amine such as diisopropylethylamine, or also pyridine. If Z is hydroxy high temperatures and/or addition of dehydrating agents are required. Useful dehydrating agents are for example acid halogenides, acid anhydrides, carbodiimides and activated azines. Typically the reaction is performed in two steps. Activation of a carboxylic acid R$^1$Z (IIIa), optional transformation of the resulting activated acid into a more stable intermediate, followed by reaction with the amine of formula (II).

In case of unactivated coupling partners method B) is referred to as Buchwald-Hartwig reaction, and corresponding reaction conditions may be chosen. If R$^1$ represents an activated phenyl or heteroaryl residue the transformation does not require transition metal catalysis.

Method C), wherein M represents a dihydroxy- or dialkoxy-boron group, is also known under the name of Suzuki reaction, and corresponding reaction conditions are well known in the art. The reaction is preferably carried out in a dipolar aprotic solvent such as dimethyl formamide, or in a polar ether, e.g. tetrahydrofuran or dimethoxyethane, in the presence of a soluble palladium(0) or related metal catalyst, for example tetrakis-(triphenylphosphine)palladium. When M represents a trialkoxy-silicon group the reaction is performed in the presence of a palladium catalyst and a fluoride source. Typically bis(dibenzylideneacetone)palladium Pd(dba)$_2$ is used in the presence of tetrabutyl-ammonium fluoride.

If one or more other functional groups, for example carboxy, hydroxy or amino, are or need to be protected in a compound of formulas (II) to (V), because they should not take part in the reaction, these are such protecting groups as are usually applied in the synthesis of amides, in particular peptide compounds, cephalosporins, penicillins, nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, "Protective Groups in Organic Synthesis", Wiley, New York.

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

In the conversion of an obtainable compound of formula (I) into another compound of formula (I), an amino group may be alkylated or acylated to give the correspondingly substituted compounds. Alkylation may be performed with an alkyl halide or an activated alkyl ester. For methylation, diazomethane may be used. Alkylation may also be performed with an aldehyde under reducing conditions. For acylation the corresponding acyl chloride is preferred. Alternatively, an acid anhydride may be used, or acylation may be accomplished with the free acid under conditions used for amide formation known per se in peptide chemistry, e.g. with activating agents for the carboxy group, such as 1-hydroxybenzotriazole, optionally in the presence of suitable catalysts or co-reagents. Furthermore amine may be transformed into heteroaryl and heterocyclyl under reaction conditions typical for such cyclizations.

A hydroxy group may be alkylated (etherified) or acylated (esterified) to give the correspondingly substituted compounds in a procedure related to the one described for an amino group. Alkylation may be performed with an alkyl halide or an activated alkyl ester. For methylation, diazomethane may be used. For acylation the corresponding acyl chloride or acid anhydride may be used, or acylation may be accomplished with the free acid and a suitable activating agent.

Reduction of a nitro group in a nitro-substituted aryl or heteroaryl group to give the corresponding amino group is done, e.g., with iron powder in alcohol or with other reducing agents.

A carboxy group in a carboxy-substituted aryl or heteroaryl group may be amidated under conditions used for amide formation known per se in peptide chemistry, e.g. with the corresponding amine and an activating agent for the carboxy group, such as 1-hydroxy-benzotriazole, optionally in the presence of suitable catalysts or co-reagents.

A chloro, bromo or iodo substitutent in an aryl or heteroaryl group may be replaced by phenyl or a phenyl derivative by reaction with a suitable phenylboronic acid in a Suzuki reaction as described under method B).

Salts of a compound of formula (I) with a salt-forming group may be prepared in a manner known per se. Acid addition salts of compounds of formula (I) may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

It should be emphasized that reactions analogous to the conversions mentioned in this chapter may also take place at the level of appropriate intermediates.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to +60° C., at −20 to +40° C., at room temperature, or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and further processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula (I) is prepared according to or in analogy to the processes and process steps defined in the Examples.

The compounds of formula (I), including their salts, are also obtainable in the form of hydrates, or their crystals can include for example the solvent used for crystallization, i.e. be present as solvates.

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of formula (II) to (V) are known, commercially available, or can be synthesized in analogy to or according to methods that are known in the art.

Starting materials of formula (II) are, for example, prepared according to the Suzuki reaction of method C) using a compound of formula (IV) and an arylboronic acid of formula (V), wherein $R^1$ is hydrogen.

Starting materials of formula (IV) are available in a Buchwald reaction between 3,5-dihalopyridine or 3,5-dihalopyrazine and an aniline carrying substituents $R^7$ and $OR^B$. The reaction is performed in the presence of a suitable palladium catalyst such as $Pd(dba)_2$, a further ligand, typically a mono- or bidentate phosphine derivative, and a strong base such as sodium tert-butoxide. The reaction is easily controlled such as to avoid diamination of the dihalopyridine or dihalopyrazine.

Metalated compounds of formula (V) are commercially available or can be prepared from the corresponding phenyl halide. In case of M representing dialkoxyboron, compounds of formula (V) are obtained by Suzuki reaction of the corresponding phenyl halogenide with $B_2(OR)_4$. If M stands for trialkoxysilicon the compound is prepared by transition metal catalyzed coupling of a phenyl halide with a silylhydride $HSi(OR)_3$.

Pharmaceutical Preparations, Methods, and Uses

The present invention relates also to pharmaceutical compositions that comprise a compound of formula (I) as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula (I), a tautomer, a prodrug or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, in particular in a method of treating neoplastic disease, autoimmune disease, transplantation related pathology and/or degenerative disease, especially those mentioned hereinabove.

The invention relates also to processes and to the use of compounds of formula (I) thereof for the preparation of pharmaceutical preparations which comprise compounds of formula (I) as active component (active ingredient).

A pharmaceutical composition for the prophylactic or especially therapeutic management of a neoplastic disease, autoimmune disease, transplantation related pathology and/or degenerative disease, of a warm-blooded animal, especially a human or a commercially useful mammal requiring such treatment, comprising a novel compound of formula (I) as active ingredient in a quantity that is prophylactically or especially therapeutically active against the said diseases, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lipsticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy-ethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a neoplastic disease, autoimmune disease, transplantation related pathology and/or degenerative disease, which comprises administering a compound of formula (I) or a pharmaceutically acceptable salt thereof, wherein the radicals and symbols have the meanings as defined above for formula (I), in a quantity effective against said disease, to a warm-blooded animal requiring such treatment. The compounds of formula (I) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

Especially, the invention provides a method for the treatment of a neoplastic disease, autoimmune disease, transplantation related pathology and/or degenerative disease, which comprises administering a compound of formula (I) as defined hereinbefore, including the compounds wherein A is CH, $R^1$ is C(=O)$R^9$ or S(=O)$_2R^{10}$, $R^3$, $R^4$, $R^5$, $R^6$ and $R^7$ are all hydrogen, $R^8$ is methyl, and $R^9$ or $R^{10}$, respectively, is methyl, or of a prodrug or a pharmaceutically acceptable salt thereof, in a quantity effective against said disease, to a warm-blooded animal requiring such treatment.

The preferred dose quantity, composition, and preparation of pharmaceutical formulations (medicines) which are to be used in each case are described above.

The present invention relates also to the use of a compound of formula (I), or a pharmaceutically acceptable salt thereof, especially a compound of formula (I) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, in particular a neoplastic disease, autoimmune disease, transplantation related pathology and/or degenerative disease.

Especially, the invention relates to the use of a compound of formula (I) as defined hereinbefore, including the compounds wherein A is CH, $R^1$ is C(=O)$R^9$ or S(=O)$_2R^{10}$, $R^3$, $R^4$, $R^5$, $R^6$ and $R^7$ are all hydrogen, $R^8$ is methyl, and $R^9$ or $R^{10}$, respectively, is methyl, or of a prodrug or a pharmaceutically acceptable salt of such a compound for the preparation of a pharmaceutical composition for the treatment of a neoplastic disease, autoimmune disease, transplantation related pathology and/or degenerative disease.

The following Examples serve to illustrate the invention without limiting the invention in its scope.

EXAMPLES

Abbreviations: dba=dibenzylidene-acetone; DMF=dimethyl formamide; DMSO=dimethyl sulfoxide; eq.=equivalent(s); m.p. melting point; MS=mass spectrum; r.t.=room temperature; RT=retention time in minutes; THF=tetrahydrofuran.

Example 1

3-(m-Mesylaminophenyl)-5-(p-methoxyphenylamino)pyridine

To a stirred solution of 3-(m-aminophenyl)-5-(p-methoxyphenylamino)pyridine (107 mg, 0.37 mmol) in pyridine (2 ml) mesyl chloride (42 mg, 0.37 mmol) is added at −20° C. The reaction mixture is allowed to warm to room temperature and stirred for additional 2 hours. The mixture is concentrated in vacuo before partitioning between water and ethyl acetate. The organic phase is separated, dried and concentrated to give the title compound in crude form. Recrystallization yields the pure compound showing a m.p. of 240° C.; $^1$H NMR (400 MHz, $d_6$-DMSO): δ 10.02 (s, 1H), 9.11 (s, 1H), 8.39 (s, 1H), 8.20 (s, 1H), 7.86 (s, 1H), 7.49 (m, 3H), 7.31 (m, 1H), 7.25 (d, J=8.84 Hz, 2H), 6.99 (d, J=8.76 Hz, 2H), 3.76 (s, 3H), 3.07 (s, 3H); MS: (M+H)$^+$ 370.4.

Example 1a 3-(m-Aminophenyl)-5-(p-methoxyphenylamino)pyridine

A stirred solution of 3-bromo-5-(p-methoxyphenylamino)pyridine (0.5 g, 1.8 mmol), 3-aminophenyl boronic acid (0.28 g, 1.8 mmol) and Na$_2$CO$_3$ (0.56 g, 5.3 mmol) in dimethoxyethane (10 ml) and water (3.5 ml) is deoxygenated using argon before adding Pd(PPh$_3$)$_4$ (0.06 g) and heating the mixture at reflux for 16 hours. The mixture is diluted with ethyl acetate, washed with brine, dried over Na$_2$SO$_4$ and concentrated. The residue is chromatographed on silicagel to afford the product; $^1$H NMR (400 MHz, $d_6$-DMSO): δ 8.16 (m, 2H), 8.10 (s, 1H), 7.34 (m, 1H), 7.10 (m, 3H), 6.91 (d, J=8.84 Hz, 2H), 6.75 (s, 1H), 6.71 (m, 1H), 6.57 (m, 1H), 5.21 (br s, 2H), 3.73 (s, 3H).

Example 1b

3-Bromo-5-(p-methoxyphenylamino)pyridine

A mixture of 3,5-dibromopyridine (1.5 g, 6.3 mmol), p-anisidine (0.94 g, 7.60 mmol), (R)-(+)-2,2'-bis(diphenylphosphino)-1,1'-binapthyl (0.16 g, 0.25 mmol) and sodium tert-butoxide (0.85 g, 8.86 mmol) in toluene (15 ml) is deoxygenated using argon before adding Pd$_2$(dba)$_3$ (0.116 g, 0.13 mmol) and heating the mixture at 70° C. for 16 hours. The mixture is diluted with diethyl ether, washed with brine, dried over Na$_2$SO$_4$ and concentrated. The residue is chromatographed on silicagel to afford the product; $^1$H NMR (400 MHz, CDCl$_3$): δ 8.16 (d, J=2.42 Hz, 1H), 8.04 (d, J=1.82 Hz, 1H), 7.30 (m, 1H), 7.09 (m, 2H), 6.90 (m, 2H), 5.89 (s, 1H), 3.81 (s, 3H).

Example 2

3-(m-Benzoylaminophenyl)-5-(p-methoxyphenylamino)pyridine

To a stirred solution of 3-(m-aminophenyl)-5-(p-methoxyphenylamino)pyridine (Example 1b, 50 mg, 0.17 mmol) in pyridine (1 ml) benzoyl chloride (24 mg, 0.17 mmol) is added at 0° C., and the mixture stirred for 15 minutes. The mixture is concentrated in vacuo before partitioning between water and ethyl acetate. The organic phase is separated, dried and concentrated to give the title compound in crude form. The crude material is purified by column chromatography on silicagel to give the title compound; m.p. 135-140° C.; $^1$H NMR (400 MHz, $d_6$-DMSO): δ 10.36 (s, 1H), 8.22 (m, 3H), 8.04 (s, 1H), 7.97 (m, 2H), 7.85 (m, 1H), 7.60 (m, 1H), 7.55 (m, 2H), 7.45 (m, 2H), 7.38 (m, 1H), 7.14 (d, J=8.76 Hz, 2H), 6.92 (d, J=8.80 Hz, 2H), 3.73 (s, 3H); MS: (M+H)$^+$ 396.1.

Example 3

5-(p-Methoxyphenylamino)-3-(m-[2-pyridylamino]phenyl)pyridine

To a stirred solution of 3-(m-aminophenyl)-5-(p-methoxyphenylamino)pyridine (Example 1b, 70 mg, 0.24 mmol) in toluene (4 ml) 2-bromopyridine (32 mg, 0.20 mmol) is added followed by (R)-(+)-2,2'-bis(diphenylphosphino)-1,1'-binaphthyl (5 mg, 0.08 mmol) and sodium tert-butoxide (30 mg, 0.28 mmol). The reaction mixture is deoxygenated by passing argon, then Pd$_2$(dba)$_3$ (4 mg, 0.04 mmol) is added and the reaction mixture is stirred for 16 h at 70° C. After cooling the reaction mixture is taken up in diethyl ether and washed with brine. The organic layer is dried over sodium sulfate and concentrated under reduced vacuum. The residue is purified on silicagel to afford the product, m.p. 161-165° C. $^1$H NMR (400 MHz, DMSO-d$_6$): δ 9.16 (br s, 1H), 8.18 (m, 4H), 7.94 (br s, 1H), 7.72 (d, J=7.9 Hz, 1H), 7.57 (t, J=7.7 Hz, 1H), 7.42 (s, 1H), 7.34 (t, J=7.8 Hz, 1H), 7.13 (t, J=8.7 Hz, 3H), 6.93 (d, J=8.8 Hz, 2H), 6.84 (d, J=8.4 Hz, 1H), 6.75 (t, J=6.2 Hz, 1H), 3.73 (s, 3H); MS: (M+H)$^+$ 369.4.

The following compounds were synthesized accordingly:

TABLE 1

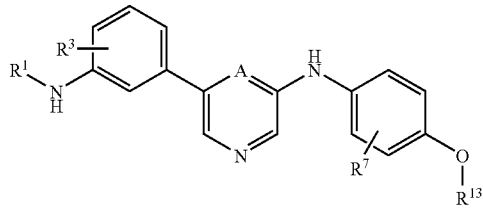

| Example | R$^1$ | R$^3$ | R$^7$ | R$^{13}$ | A | m.p. |
|---|---|---|---|---|---|---|
| 4 | ethylsulfonyl | H | H | Me | CH | 160-165° C. |
| 5 | isopropylsulfonyl | H | H | Me | CH | 200-204° C. |
| 6 | 4-methylphenylsulfonyl | H | H | Me | CH | 170° C. |
| 7 | 3-chloropropylsulfonyl | H | H | Me | CH | 150° C. |
| 8 | acetyl | H | H | Me | CH | 165-170° C. |
| 9 | 4-methoxybenzoyl | H | H | Me | CH | 176-178 |
| 10 | 2-ethoxybenzoyl | H | H | Me | CH | 155-160° C. |
| 11 | 2-chloropyridine-3-carbonyl | H | H | Me | CH | 160° C. |

TABLE 1-continued

| Example | R¹ | R³ | R⁷ | R¹³ | A | m.p. |
|---|---|---|---|---|---|---|
| 12 | 2-acetylpyrazine | H | H | Me | CH | 120° C. |
| 13 | 3-acetylpyridine | H | H | Me | CH | 218-220° C. |
| 14 | 2-acetylfuran | H | H | Me | CH | 180° C. |
| 15 | phenylacetone | H | H | Me | CH | 155-160° C. |
| 16 | 4-acetylpyridine | H | H | Me | CH | 130-135° C. |
| 17 | 2-acetylpyridine | H | H | Me | CH | 140-145° C. |
| 18 | 2'-chloroacetophenone | H | H | Me | CH | 210° C. |
| 19 | 3'-chloroacetophenone | H | H | Me | CH | 140° C. |
| 20 | pinacolone | H | H | Me | CH | 188-190° C. |

TABLE 1-continued

| Example | R¹ | R³ | R⁷ | R¹³ | A | m.p. |
|---|---|---|---|---|---|---|
| 21 | propanoyl (ethyl ketone) | H | H | Me | CH | 182-184° C. |
| 22 | 2-thienylcarbonyl | H | H | Me | CH | 206-208° C. |
| 23 | phenylsulfonyl | H | H | Me | CH | 208-210° C. |
| 24 | benzyl | H | H | H | CH | 160-165° C. |
| 25 | 3-methoxybenzoyl | H | H | Me | CH | 170° C. |
| 26 | isobutyryl | H | H | Me | CH | 175° C. |
| 27 | benzoyl | H | H | benzyl | CH | 180° C. |
| 28 | benzylsulfonyl | H | H | Me | CH | 190° C. |
| 29 | benzoyl | H | 3-OMe | Me | CH | 60° C. |
| 30 | benzoyl | H | 2-OMe | Me | CH | 70° C. |

TABLE 1-continued
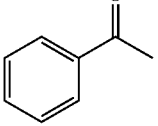
| Example | R¹ | R³ | R⁷ | R¹³ | A | m.p. |
|---|---|---|---|---|---|---|
| 31 | 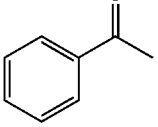 | H | H | Et | CH | solid |
| 32 | 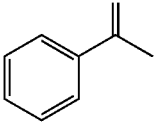 | H | H | Allyl | CH | 140° C. |
| 33 | 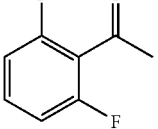 | H | H | i-Pr | CH | 161° C. |
| 34 | 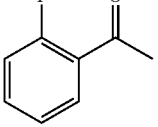 | H | H | Me | CH | 188-194° C. |
| 35 | 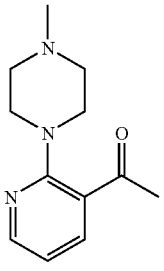 | H | H | Me | CH | 161-165° C. |
| 36 | 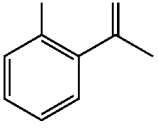 | H | H | Me | CH | 60-62° C. |
| 37 | 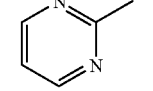 | H | H | Me | CH | 140° C. |
| 38 |  | H | H | Me | CH | 121° C. |

TABLE 1-continued

| Example | R¹ | R³ | R⁷ | R¹³ | A | m.p. |
|---|---|---|---|---|---|---|
| 39 | 1-methylimidazol-2-yl C(=O) | H | H | Me | CH | 160° C. |
| 40 | 2-aminopropanoyl·HCl | H | H | Me | CH | 122-130° C. |
| 41 | methoxyacetyl | H | H | Me | CH | 140-141° C. |
| 42 | benzoyl | H | H | Me | N | 180-182° C. |
| 43 | 2-(diethylamino)pyridine-3-carbonyl | H | H | Me | CH | 120° C. |
| 44 | pyridine-4-carbonyl | H | H | Me | N | 205-210° C. |
| 45 | 2-fluorobenzoyl | H | H | Me | N | 141-145° C. |
| 46 | 2-morpholinobenzoyl | H | H | Me | N | 188-194° C. |

TABLE 1-continued

[Structure: R¹-NH-(phenyl with R³)-A-(pyrazine with N)-NH-(phenyl with R⁷)-O-R¹³]

| Example | R¹ | R³ | R⁷ | R¹³ | A | m.p. |
|---------|-----|------|-----|------|------|------|
| 47 | 3-acetylpyridine (pyridin-3-yl-C(O)-) | 4-Me | H | Me | CH | |
| 48 | phenyl-C(O)- (acetophenone) | 4-Me | H | Me | CH | |
| 49 | MeO-CH₂-C(O)- | 4-Me | H | Me | CH | |
| 50 | CH₃-CH(NH₃Cl)-C(O)- | 4-Me | H | Me | CH | |
| 51 | (1-methylimidazol-2-yl)-C(O)- | 4-Me | H | Me | CH | |
| 52 | 2-methylpyrimidin-yl | 4-Me | H | Me | CH | |
| 53 | 2-(COOH)phenyl-C(O)- | 4-Me | H | Me | CH | |
| 54 | 2-methylpyridin-yl | 4-Me | H | Me | CH | |
| 55 | 2-methyl-3-cyanopyridin-yl | 4-Me | H | Me | CH | |
| 56 | 2-methyl-3-chloropyridin-yl | 4-Me | H | Me | CH | |

TABLE 1-continued

| Example | R¹ | R³ | R⁷ | R¹³ | A | m.p. |
|---|---|---|---|---|---|---|
| 57 | 2-Me, 3-CF₃ pyridinyl | 4-Me | H | Me | CH | |
| 58 | 3-Me pyrazinyl | 4-Me | H | Me | CH | |
| 59 | 4-Me, 3-Cl 1,2,5-thiadiazolyl | 4-Me | H | Me | CH | |
| 60 | 3-Me pyridazinyl | 4-Me | H | Me | CH | |
| 61 | 4-Me pyrimidinyl | 4-Me | H | Me | CH | |
| 62 | 6-Cl, 2-Me pyridinyl | 4-Me | H | Me | CH | |
| 63 | 2-Me, 3-COOMe pyridinyl | 4-Me | H | Me | CH | |
| 64 | 4-Me pyridinyl | 4-Me | H | Me | CH | |
| 65 | 3-Me, 2-Cl pyrazinyl | 4-Me | H | Me | CH | |
| 66 | 4-tBu, 2-Me thiazolyl | 4-Me | H | Me | CH | |

Example 67

Cell Cultures and Cell Lines

Cell lines are cultured in RPMI-1640 tissue culture medium containing either 5% or 10% fetal calf serum, 0.05 mM 2-mercaptoethanol, 2 mM glutamine and penicillin/streptomycin 50 µg/ml (complete medium) (Sigma, Buchs, Switzerland). General growth conditions are 37° C. and 7.5% $CO_2$.

The following mouse cell lines (either EGFP transfected or not) are being used: A20.2J (ATCC: TIB-208), MC57G (ATCC: CRL-2295).

The following human cell lines (either EGFP transfected or not) are being used: HeLa (ATCC: CCL-2), KB (ATCC: CCL-17), MCF7 (ATCC: HTB-22), SK-BR-3 (ATCC: HTB-30), SK-Mel 1 (ATCC: HTB-67), SK-Mel 28 (ATCC: HTB-72), PC-3 (ATCC: CRL-1435), SW 480 (ATCC: CCL-228), NCI-H460 (ATCC: HTB-177), NCI-H1792 (ATCC: CRL-5895), HT1080 (ATCC: CCL-21), Jurkat (ATCC: TIB-152), Ramos (ATCC: CRL-1596), Raji (ATCC: CCL-86), H9 (ATCC: HTB-176), Hut78 (ATCC: TIB-161), K562 (ATCC: CCL 243), HL-60 (ATCC: CCL 240), U-87MG (ATCC: HTB-14), HepG2 (ATCC: HB-8065), U-2 OS (ATCC: HTB-96), Saos-2 (ATCC: HTB-85), U937 (ATCC: CRL 1593), Hs 578T (ATCC: HTB 126), HBL-100 (ATCC: HTB 124), Molt-4 (ATCC: CRL 1582).

As control cells primary human fibroblasts, primary human keratinocytes or freshly prepared human peripheral blood leucocytes (PBL) are being used.

Example 68

Primary Screening Setup

All the manipulations are performed under sterile conditions. The assays are being performed in commercially available 96 or 384 well flat bottom clear microtiter plates (Greiner, Germany) respectively, which are suitable for tissue culture techniques. A defined number of EGFP transfected adherent test cells (96 well plates: $10^4$-$10^5$, 384 well plates: 1500–$2*10^4$) are plated out 24 h before treatment either in 75 µl (96 well plates) or 60 µl (384 well plates) complete medium per well in order to ensure appropriate cell spreading. For this purpose a peristaltic pump (e.g. Multidrop by Thermo-Labsystems, Finland) or another suitable device is used. Cells in suspension are plated out according to the same procedure but 1 h prior to treatment. Between seeding out and treatment or addition of compounds the cells are incubated at 37° C. under 7.5% $CO_2$. Subsequently, the compounds under investigation are added at defined concentrations (40-80 µM in either 25 µl (96 well plates) or 20 µl (384 well plates) complete medium containing max 4% DMSO) with an appropriate device (e.g. liquid handling system, multi channel pipette etc.) resulting in a final concentration in the test well of 10-20 µM compound in max 1% DMSO.

Immediately after the addition of the compounds to the cells the zero fluorescence value (t=0 h) is determined by using a fluorescence microplate reader in order to be able to normalize the fluorescence activities. Afterwards, the test plates are further incubated for a total of 48 h at 37° C. under 7.5% $CO_2$ and are shortly removed only for the purpose of measurement at 8 h, 24 h and 48 h, respectively.

Example 69

Measurement and Quantification of the Primary Screening

Relative fluorescence activities of EGFP in compound treated test cells in relation to control cells and cells treated with standard drugs are measured by using a BMG Fluostar microplate fluorescence reader equipped with a filter pair for excitation/emission at 485 nm/520 nm. The optimum signal to noise ratio is detected by using the time-resolved mode of measurement with a delay of 20 µs and an integration time over 1 ms. The gain is adjusted in such a way that the control cells produce a fluorescence activity of 90% of the maximum. Kinetics is performed by measuring the relative fluorescence activities at t=0 h, 8 h, 24 h and 48 h. Crude fluorescence activities are individually normalized for different cell numbers and various optical activities of the test compounds/plate-wells by dividing each value from t=8 h, 24 h and 48 h by the value of t=0 h resulting in E(8), E(24) and E(48) values. Subsequently, the E(x) values are further processed by forming the inverse (Q-value) of the products $E(8)*E(24)*E(48)$ which result in numbers>1 for apoptotic/necrotic activities of the compounds and numbers<1 for proliferative activities of the compounds. Controls (untreated) show values similar to 1. Compounds producing Q values>2 are being considered relevant in terms of apoptotic/necrotic activity and are subsequently tested in the secondary screening setup.

Example 70

Secondary Screening Setup

All the manipulations are performed under sterile conditions. The assays are being performed in case of adherent cells in commercially available 24 well flat bottom tissue culture plates (Greiner, Germany) and in case of suspension cells in polypropylene tubes (P-tubes) 1.4 ml (Matrix, UK), respectively.

Adherent test cells: $2*10^4$-$4*10^4$ of EGFP transfected cells in 0.5 ml complete medium are plated out 24 h before treatment. At t=0 the medium is removed and 450 µl new complete medium is added. Subsequently, 50 µl complete medium containing the test compound in max. 5% DMSO is added resulting in final concentrations of 20 µM, 10 µM, 3 µM, 1 µM and 0.3 µM of the test compounds, respectively. After 48 h incubation the cells are harvested and analyzed with fluorescence activated cell scanning device (FACSCalibur™, BD Biosciences) according to standard procedures.

Suspension cells: $10^5$ test cells in 450 µl complete medium are pipetted into P-tubes. 50 µl complete medium containing the compounds (see adherent cells) is added immediately. After 48 h of incubation the test cells are analyzed directly on a FACSCalibur™.

Example 71

Quantification of the Secondary Screening

By monitoring the EGFP fluorescence activity in FL1 on a FACSCalibur™, it is possible to distinguish between proliferating cells, apoptotic cells and necrotic cells within the same cell population. The proliferating cells show a high GFP fluorescence activity, the apoptotic population shows an intermediate fluorescence activity whereas the necrotic cells demonstrate a residual fluorescence activity comparable to mock-transfected cells. Within the CellQuest Software (BD Biosciences) three regions are defined in the histogram: M1 comprising the proliferating cells, M2 comprising the apoptotic cell population and M3 comprising the necrotic cell population. As readout the relative abundance of the cells belonging either to M1, M2 or M3 are expressed. Compounds inducing M2 values>50% and M3 values<30% are being considered relevant and are further tested and characterized in the tertiary/advanced screening setup.

Example 72

Tertiary Screening Setup

A) Hoechst 33342 Nuclear Staining

This assay is performed in 96 well tissue culture plates. Appropriate number of cells (adherent cells: $3-5*10^3$, suspension cells: $8-10*10^3$) are being seeded out in 80 µl complete medium. Adherent cells are incubated for 24 h for proper spreading out before addition of test compounds while suspension cells are immediately treated with test compounds after seeding out. The test compounds are added in 20 µl complete medium containing max 5% DMSO. The final compound concentrations in the assays are in the range of 0.001 µM-10 µM. After 24 h or 48 h incubation at culture conditions, 10 µl medium containing Hoechst 33342 dye (Sigma B-2261) at 2-5 µg/ml are added to each well. The assay plates are then further incubated for 30 minutes and subsequently analyzed with a standard inverted fluorescence microscope.

The readout allows the determination of the fraction of apoptotic nuclei as well as other morphological criteria specific for apoptosis as a function of the treatment. Results are indicated in Table 2. The scores A, B, C and D are explained at the end of the Table.

TABLE 2

| Hoechst 33342 nuclear staining (48 h read-out) | | | | | |
|---|---|---|---|---|---|
| Example | Jurkat | Jily | PBL | HeLa | MRC5 |
| 1 | C | C | D | C | C |
| 2 | B | B | D | B | D |
| 3 | B | B | D | C | C |
| 4 | B | B | D | C | B |
| 5 | B | B | D | C | C |
| 6 | C | C | D | C | C |
| 7 | B | B | D | B | B |
| 8 | C | C | D | C | C |
| 10 | B | C | D | B | D |
| 11 | B | B | D | B | B |
| 12 | B | B | D | B | C |
| 13 | C | C | D | C | D |
| 14 | B | B | D | C | C |
| 15 | C | C | D | C | D |
| 16 | A | A | D | B | A |
| 17 | C | B | D | B | D |
| 18 | A | A | D | B | B |
| 19 | C | C | D | C | D |
| 20 | C | C | D | C | D |
| 21 | C | C | D | C | D |
| 22 | B | B | D | B | C |
| 23 | C | C | D | C | D |
| 24 | D | D | D | C | C |
| 25 | C | D | D | D | D |
| 26 | B | C | D | C | D |
| 27 | D | D | D | D | D |
| 28 | D | D | D | D | D |
| 29 | C | C | D | C | D |
| 30 | C | C | D | D | D |
| 34 | C | C | C | C | C |

TABLE 2-continued

| Hoechst 33342 nuclear staining (48 h read-out) | | | | | |
|---|---|---|---|---|---|
| Example | Jurkat | Jily | PBL | HeLa | MRC5 |
| 36 | D | D | D | D | D |
| 41 | C | C | C | C | D |

A: EC50 < 0.01 µM;
B: 0.01 µM < EC50 < 0.1 µM;
C: 0.1 µM < EC50 < 1 µM
D: EC50 > 1 µM
n.d.: not determined B) MTS Proliferation Assay The assay is performed in 96 well tissue culture plates. The cells (range: $1.5*10^3-10^4$) are seeded out in 80 µl complete medium 24 h prior to compound treatment. The test compounds are added in 20 µl complete medium containing max 5% DMSO. The final compound concentrations in the assays are in the range of 0.001 µM-10 µM. The assay plates are incubated for 72 h at culture conditions. The MTS reagent is prepared according to the manufacturer's protocol (Promega G1111). 20 µl MTS reagent are added to each well, the assay plates are quickly spun and incubated for another 3 h at culture conditions. Subsequently, the plates are shortly shaked and absorption measured with a microplate-reader at 492 nm. $IC_{50}$ values are determined by graphical analysis and are indicated in Table 3. The scores A, B, C and D are explained at the end of the Table.

TABLE 3

| MTS proliferation assay (72 h read-out) | | | | | |
|---|---|---|---|---|---|
| Example | Jurkat | Jily | HeLa | MRC5 | HT1080 |
| 1 | B | B | C | C | C |
| 2 | A | A | B | B | B |
| 3 | B | B | C | C | B |
| 4 | B | B | C | C | B |
| 5 | B | B | C | C | C |
| 6 | C | C | C | C | C |
| 7 | B | B | C | C | C |
| 8 | C | C | C | D | C |
| 9 | C | C | C | D | C |
| 10 | B | B | C | C | B |
| 11 | B | B | B | B | B |
| 12 | A | B | B | C | B |
| 13 | B | B | C | C | C |
| 14 | B | B | C | C | C |
| 15 | C | C | C | C | C |
| 16 | n.d. | n.d. | B | A | A |
| 17 | A | B | B | B | B |
| 18 | A | A | B | A | A |
| 19 | C | C | C | C | C |
| 20 | C | C | C | D | C |
| 21 | B | C | C | C | C |
| 22 | B | B | B | C | B |
| 23 | C | C | C | C | C |
| 24 | C | C | C | C | C |
| 25 | C | C | D | D | D |
| 26 | B | B | C | C | C |
| 27 | D | D | D | D | D |
| 28 | D | D | D | D | D |
| 29 | C | C | D | D | D |
| 30 | C | C | D | D | D |

A: IC50 < 0.01 µM;
B: 0.01 µM < IC50 < 0.1 µM;
C: 0.1 µM < IC50 < 1 µM
D: IC50 > 1 µM
n.d.: not determined C) PI Staining for Cell Cycle Distribution $1-2*10^5$ cells are seeded into 24 well tissue culture plates and incubated for 24 h prior to compound addition. Compounds are added for 24 h in a final concentration of 3 μM or 10 μM. Adherent cells are harvested by trypsinization. The cell suspensions are fixed by adding 2 parts ice cold ethanol 100% while vortexing. Then the samples are stored for >2 h at −20° C. Subsequently the cells are washed with PBS once and resuspended in 250 μl PBS containing 50 μg/ml PI (Calbiochem #537059), then the samples are incubated at 37° C. for 30 minutes and subsequently analyzed on a FACSCalibur™ monitoring linear PI fluorescence activity on FL2. The readout allows the detection of a possible direct or indirect influence of the tested compounds on the cell cycle. All active test compounds induce an arrest of the cell population in the G2M phase. This effect has been quantified by running the test at different concentrations. In Table 4 EC50 values are tabulated.

TABLE 4

PI staining for cell cycle distribution (24 h read-out)

| Example | HeLa | Jurkat |
|---------|------|--------|
| 1  | C | |
| 2  | C | |
| 4  | C | |
| 5  | C | |
| 7  | C | |
| 11 | A | |
| 16 | B | |
| 18 | A | |

A: EC50 < 0.01 μM;
B: 0.01 μM < EC50 < 0.1 μM;
C: 0.1 μM < EC50 < 1 μM
D: EC50 > 1 μM
n.d.: not determined D) Mitochondrial Membrane Potential This assay is performed in 96 well tissue culture plates. Appropriate number of cells (adherent cells: $3-5*10^3$, suspension cells: $8-10*10^3$) are being seeded out in 80 μl complete medium. Adherent cells are incubated for 24 h for proper spreading out before addition of test compounds while suspension cells are immediately treated with test compounds after seeding out. The test compounds are added in 20 μal complete medium containing max 5% DMSO. The final compound concentrations in the assays are in the range of 0.001 μM-10 μM dependent on the potency of the compounds under investigation. After 24 h or 48 h incubation at culture conditions, 10 μl medium containing JC-1 (Molecular Probes, T-3168) at 2-5 μg/ml are added to each well. The assay plates are then further incubated for 30 minutes and subsequently analyzed with a standard inverted fluorescence microscope by using the FITC and TRITC filters. Cells with an intact mitochondrial membrane potential (mmp) show an orange staining (visualized with the TRITC filter) while cells with a perturbed or missing mmp demonstrate a green staining (visualized with the FITC filter).

The readout allows the determination of the fraction of cells which show a dissipation of the mitochondrial membrane potential strongly indicating an apoptotic cell death as a function of the treatment. Results are indicated in Table 5. The scores A, B, C and D are explained at the end of the Table.

TABLE 5

Mitochondrial membrane potential (48 h read-out)

| Example | Jurkat | DOHH2 | PBL | HeLa | MCF7 |
|---------|--------|-------|-----|------|------|
| 1  | C | C | D | C | D |
| 2  | B | B | D | B | D |
| 3  | B | B | D | C | C |
| 4  | A | A | D | C | D |
| 5  | A | B | D | C | D |
| 6  | C | C | D | D | D |
| 7  | B | B | D | C | D |
| 8  | C | C | D | C | D |
| 9  | B | B | D | C | C |
| 10 | B | C | D | C | C |
| 11 | B | B | D | B | D |
| 12 | B | B | D | C | C |
| 13 | B | C | D | C | D |
| 14 | B | B | D | C | D |
| 15 | B | C | D | C | D |
| 16 | A | A | D | B | C |
| 17 | B | B | D | B | D |
| 18 | B | B | D | B | C |
| 19 | C | C | D | C | D |
| 20 | C | C | D | C | D |
| 21 | C | C | D | C | D |
| 22 | B | B | D | B | C |
| 23 | C | C | D | C | C |
| 24 | D | D | D | C | C |
| 25 | C | D | D | D | D |
| 26 | C | C | D | D | D |
| 27 | D | D | D | D | D |
| 28 | C | C | D | D | D |
| 29 | C | D | D | D | D |
| 30 | D | D | D | D | D |
| 36 | D | D | D | D | D |
| 41 | C | C | C | C | C |

A: EC50 < 0.01 μM;
B: 0.01 μM < EC50 < 0.1 μM;
C: 0.1 μM < EC50 < 1 μM
D: EC50 > 1 μM
n.d.: not determined E) Colony Forming Units Appropriate numbers of cells (100-150 cells, dependent on the cell type) are being seeded out in 1 ml complete medium into 6-well plates and allowed to attach for 48 h. The compounds are added after 48 h in 500 μl solution. The concentrations are in the range of 0.001 μM-3 μM. Control plates receive the same volume of medium containing the appropriate amount of DMSO. The plates are incubated for 6 days at cell culture conditions and subsequently scored for growth of colonies (containing more than 30 cells) by using a microscope. $IC_{50}$ values are determined by graphical analysis and are indicated in the Table 6 in μM concentration.

TABLE 6

Colony Forming Units (read-out after 6 days)

| Example | HeLa | H460 |
|---------|------|------|
| 2 | C | C |
| 4 | B | B |

A: EC50 < 0.01 μM;
B: 0.01 μM < EC50 < 0.1 μM;
C: 0.1 μM < EC50 < 1 μM
D: EC50 > 1 μM
n.d.: not determined

What is claimed:
1. Compounds of formula (I)

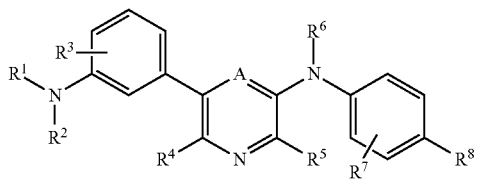

wherein A is CH or C-lower alkyl;
$R^1$ represents C(=O)$R^9$, S(=O)$_2R^{10}$, P(=O)(O$R^{11}$)$_2$, optionally substituted phenyl or optionally substituted heteroaryl;
$R^2$ represents hydrogen or lower alkyl;
$R^3$ represents one or two substituents independently selected from the group consisting of hydrogen, lower alkyl, cycloalkyl, heterocyclyl, hydroxy-lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkyl-sulfinyl, alkylsulfonyl, arylsulfonyl, heteroarylsulfonyl, hydroxy, amino, lower alkylamino, di-lower alkylamino, lower alkylcarbonylamino, lower alkylcarbonyl, optionally substituted phenylcarbonyl, carboxy, lower alkoxycarbonyl, lower alkoxy-lower alkoxycarbonyl; aminocarbonyl wherein amino is unsubstituted or mono or di-substituted with lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl, or wherein the two substituents on the amino nitrogen of the aminocarbonyl taken together with the nitrogen atom form a nitrogen containing heterocyclic ring; cyano, halogen, and nitro;
$R^4$ and $R^5$, independently of each other, represent hydrogen, lower alkyl, halo-lower alkyl, lower alkoxy, amino or halogen;
$R^6$ represents hydrogen, lower alkyl, lower alkylcarbonyl or lower alkoxycarbonyl;
$R^7$ represents one or two substituents independently selected from the group consisting of hydrogen, lower alkyl, cycloalkyl, heterocyclyl, hydroxy-lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, hydroxy, amino, lower alkyl-amino, di-lower alkylamino, lower alkylcarbonylamino, lower alkylcarbonyl, optionally substituted phenylcarbonyl, carboxy, lower alkoxycarbonyl, lower alkoxy-lower alkoxy-, carbonyl; aminocarbonyl wherein amino is unsubstituted or mono or di-substituted with lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on the amino nitrogen of the aminocarbonyl taken together with the nitrogen atom form a nitrogen containing heterocyclic ring; cyano, halogen and nitro;
$R^8$ represents hydrogen, lower alkoxy, hydroxy, lower alkyl, lower alkyl-carbonyloxy, lower alkoxy-carbonyl, aminocarbonyl, lower alkyl-aminocarbonyl, di-lower alkyl-aminocarbonyl, amino, lower alkylamino, di-lower alkylamino, halogen, cyano or nitro;
$R^9$ represents a substituent selected from the group consisting of optionally substituted cycloalkyl, optionally substituted aryl, optionally substituted heteroaryl, and optionally substituted heteroarylalkyl wherein alkyl is unsubstituted or substituted by hydroxy, lower alkyl, halo-lower haloalkyl, lower alkoxy, amino, lower alkylamino, di-lower alkylamino, lower alkyl-carbonyloxy, aminocarbonyloxy, lower alkylaminocarbonyloxy, di-lower alkylaminocarbonyloxy or halogen;
$R^{10}$ represents a substituent selected from the group consisting of cycloalkyl, optionally substituted aryl, optionally substituted heteroaryl, and optionally substituted heteroarylalkyl;
$R^{11}$ represents lower alkyl, halo-lower alkyl, lower alkoxy-lower alkyl, aryl or aryl-lower alkyl;
or pharmaceutically acceptable salts thereof.
2. Compounds of formula (I)

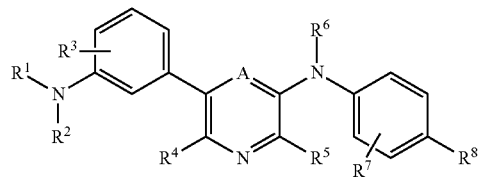

(I) wherein A is CH or C-lower alkyl;
$R^1$ represents C(=O)$R^9$, S(=O)$_2R^{10}$, P(=O)(O$R^{11}$)$_2$, optionally substituted phenyl or optionally substituted heteroaryl;
$R^2$ represents hydrogen, lower alkylcarbonyl, amino-lower alkylcarbonyl, lower alkoxycarbonyl, aryl-lower alkylcarbonyl or arylmethoxycarbonyl;
$R^3$ represents hydrogen, lower alkyl, halo-lower alkyl, lower alkoxy-lower alkyl, halo-lower alkoxy-lower alkyl, cycloalkyl, optionally substituted alkenyl, optionally substituted alkinyl, optionally substituted heteroaryl, lower alkoxy, halo-lower alkoxy, lower alkoxy-lower alkoxy, alkenyloxy, aryloxy, heteroaryloxy, cyano, halogen or nitro;
$R^4$ and $R^5$, independently of each other, represent hydrogen, lower alkyl, halo-lower alkyl, lower alkoxy or halogen;
$R^6$ represents hydrogen, lower alkyl, lower alkylcarbonyl, lower alkoxycarbonyl or aryl-lower alkoxycarbonyl;
$R^7$ represents a substituent selected from the group consisting of hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkyl mercapto, alkylsulfinyl, halo-lower alkylsulfinyl, alkylsulfonyl, arylsulfonyl, heteroarylsulfonyl, lower alkylamino, di-lower alkylamino, lower alkylcarbonyl-amino, lower alkylcarbonyl, optionally substituted phenylcarbonyl, carboxy, lower alkoxycarbonyl, lower alkoxy-lower alkoxycarbonyl; aminocarbonyl wherein amino is unsubstituted or mono or di-substituted with lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl, or wherein the two substituents on the amino nitrogen of the aminocarbonyl taken together with the nitrogen atom form a nitrogen containing heterocyclic ring; cyano, halogen, and nitro;

$R^8$ represents —$OR^{13}$ and $R^{13}$ represents a substituent selected from the group consisting of alkyl, cycloalkyl-lower alkyl, halo-lower alkyl, hydroxy-lower alkyl, lower alkoxy-lower alkyl, acyloxy-lower alkyl, lower alkoxy-lower alkoxy-lower alkyl, halo-lower alkoxy-lower alkyl, cyano-lower alkyl, carboxyalkyl, lower alkoxycarbonyl-lower alkyl; aminocarbonyl-lower alkyl wherein amino is unsubstituted or mono or di-substituted with lower alkyl, hydroxy-lower alkyl, alkoxy-lower alkyl and amino-lower alkyl, or wherein the two substituents on nitrogen form together with the nitrogen heterocyclyl; amino-lower alkyl, wherein amino is unsubstituted or mono or di-substituted with lower alkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl, or wherein the two substituents on the amino nitrogen of the amino-lower alkyl taken together with the nitrogen atom form a nitrogen containing heterocyclic ring; optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, lower alkoxycarbonyl, lower alkoxy-lower alkoxycarbonyl; aminocarbonyl wherein amino is unsubstituted or mono or di-substituted with lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heterocyclyl, optionally substituted heteroaryl-lower alkyl, or wherein the two substituents on the amino nitrogen of the aminocarbonyl taken together with the nitrogen atom form a nitrogen containing heterocyclic ring; lower alkylsulfonyl, halo-lower alkylsulfonyl, lower alkoxy-lower alkylsulfonyl, arylsulfonyl, aryl-lower alkylsulfonyl, di-lower alkylphosphonyl, and di-phenylphosphonyl;

or $R^7$ and $R^{13}$ together with two carbon atoms of the phenyl ring and oxygen represent a 5, 6 or 7-membered ring optionally containing one or two further oxygen atoms and/or one nitrogen or sulfur atom, and optionally being substituted by oxo, lower alkyl or lower alkoxy;

$R^9$ represents a substituent selected from the group consisting of cycloalkyl, optionally substituted aryl, optionally substituted heteroaryl, heteroarylalkyl, a group —C(=O)—$R^{12}$, a group —C(=NOH)—$R^{12}$ and a group —C(=NO-alkyl)-$R^{12}$;

$R^{10}$ represents a substituent selected from the group consisting of cycloalkyl, optionally substituted aryl, optionally substituted heteroaryl and heteroarylalkyl;

$R^{11}$ represents lower alkyl, halo-lower alkyl, lower alkoxy-lower alkyl, aryl or aryl-lower alkyl;

$R^{12}$ represents optionally substituted aryl or optionally substituted heteroaryl;

or pharmaceutically acceptable salts thereof.

3. Compounds of formula (I) according to claim 2, wherein A is CH;

$R^1$ represents C(=O)$R^9$, S(=O)$_2R^{10}$, P(=O)(O$R^{11}$)$_2$, optionally substituted phenyl or optionally substituted heteroaryl;

$R^2$ represents hydrogen, lower alkylcarbonyl, amino-lower alkylcarbonyl or lower alkoxycarbonyl;

$R^3$ represents hydrogen, lower alkyl, halo-lower alkyl, lower alkoxy-lower alkyl, halo-lower alkoxy-lower alkyl, cycloalkyl, optionally substituted alkenyl, optionally substituted alkinyl, optionally substituted heteroaryl, lower alkoxy, halo-lower alkoxy, lower alkoxy-lower alkoxy, alkenyloxy, aryloxy, heteroaryloxy, cyano, halogen or nitro;

$R^4$ and $R^5$ represent hydrogen;

$R^6$ represents hydrogen, lower alkylcarbonyl or lower alkoxycarbonyl;

$R^7$ represents hydrogen, lower alkyl, halo-lower alkyl, optionally substituted alkenyl, optionally substituted alkinyl, optionally substituted heteroaryl, lower alkoxy, halo-lower alkoxy, lower alkoxy-lower alkoxy, alkenyloxy, alkyl mercapto, alkylsulfinyl, halo-lower alkylsulfinyl, alkylsulfonyl, arylsulfonyl, heteroarylsulfonyl, lower alkylamino, di-lower alkylamino, lower alkylcarbonylamino, lower alkylcarbonyl, carboxy, lower alkoxycarbonyl, lower alkoxy-lower alkoxycarbonyl, cyano, halogen, or nitro;

$R^8$ represents —$OR^{13}$ and $R^{13}$ represents a substituent selected from the group consisting of alkyl, cycloalkyl-lower alkyl, halo-lower alkyl, hydroxy-lower alkyl, lower alkoxy-lower alkyl, acyloxy-lower alkyl, lower alkoxy-lower alkoxy-lower alkyl, halo-lower alkoxy-lower alkyl, cyano-lower alkyl, carboxyalkyl, lower alkoxycarbonyl-lower alkyl; aminocarbonyl-lower alkyl wherein amino is unsubstituted or mono or di-substituted with lower alkyl, hydroxy-lower alkyl, alkoxy-lower alkyl, amino-lower alkyl, or wherein the two substituents on the amino nitrogen of the aminocarbonyl-lower alkyl taken together with the nitrogen atom form a nitrogen containing heterocyclic ring; amino-lower alkyl, wherein amino is unsubstituted or mono or di-substituted with lower alkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl, or wherein the two substituents on the amino nitrogen of the amino-lower alkyl taken together with the nitrogen atom form a nitrogen containing heterocyclic ring; optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, lower alkoxycarbonyl, lower alkoxy-lower alkoxycarbonyl; aminocarbonyl wherein amino is unsubstituted or mono or di-substituted with lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heterocyclyl optionally substituted heteroaryl-lower alkyl, or wherein the two substituents on the amino nitrogen of the aminocarbonyl taken together with the nitrogen atom form a nitrogen containing heterocyclic ring; lower alkylsulfonyl, halo-lower alkylsulfonyl, lower alkoxy-lower alkylsulfonyl, arylsulfonyl, aryl-lower alkylsulfonyl, di-lower alkylphosphonyl, and di-phenylphosphonyl;

or $R^7$ and $R^{13}$ together with two carbon atoms of the phenyl ring and oxygen represent a 5, 6 or 7-membered ring optionally containing one or two further oxygen atoms and/or one nitrogen or sulfur atom, and optionally being substituted by oxo, lower alkyl or lower alkoxy;

$R^9$ represents a substituent selected from the group consisting of cycloalkyl, optionally substituted aryl, optionally substituted heteroaryl and heteroarylalkyl, and a group —C(=NO-alkyl)-$R^{12}$;

$R^{10}$ represents a substituent selected from the group consisting of cycloalkyl, optionally substituted aryl, optionally substituted heteroaryl and heteroarylalkyl;

$R^{11}$ represents lower alkyl, halo-lower alkyl, lower alkoxy-lower alkyl, aryl or aryl-lower alkyl;

$R^{12}$ represents optionally substituted aryl or optionally substituted heteroaryl;

or pharmaceutically acceptable salts thereof.

4. Compounds of formula (I) according to claim 1, wherein A is CH;

$R^1$ represents C(=O)$R^9$, S(=O)$_2R^{10}$, P(=O)(O$R^{11}$)$_2$, optionally substituted phenyl or optionally substituted heteroaryl;

$R^2$ represents hydrogen or lower alkyl;

$R^3$ represents one or two substituents independently selected from the group consisting of hydrogen, lower alkyl, cylcoalkyl, heterocyclyl, hydroxy-lower alkyl, halo-lower alkyl, lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, alkyl mercapto, alkylsulfinyl, halo-lower alkylsulfinyl, alkylsulfonyl, arylsulfonyl, heteroarylsulfonyl, hydroxy, amino, lower alkylamino, di-lower alkylamino, lower alkylcarbonylamino, lower alkylcarbonyl, carboxy, lower alkoxycarbonyl, lower alkoxy-lower alkoxycarbonyl, aminocarbonyl wherein the amino nitrogen of the aminocarbonyl is unsubstituted or substituted by one or two lower alkyl substituents wherein the two substituents on nitrogen of the aminocarbonyl taken together with the nitrogen atom form a nitrogen containing heterocyclic ring; cyano, halogen and nitro;

$R^4$ and $R^5$, independently of each other, represent hydrogen or lower alkyl;

$R^6$ represents hydrogen, lower alkyl, lower alkylcarbonyl or lower alkoxycarbonyl;

$R^7$ represents a substituent independently selected from the group consisting of hydrogen, lower alkyl, cylcoalkyl, heterocyclyl, hydroxy-lower alkyl, halo-lower alkyl, lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, alkyl mercapto, alkylsulfinyl, halo-lower alkylsulfinyl, alkylsulfonyl, arylsulfonyl, heteroarylsulfonyl, hydroxy, amino, lower alkylamino, di-lower alkylamino, lower alkylcarbonylamino, lower alkylcarbonyl, carboxy, lower alkoxycarbonyl, lower alkoxy-lower alkoxycarbonyl, aminocarbonyl wherein the amino nitrogen of the aminocarbonyl is unsubstituted or substituted by one or two lower alkyl substituents or wherein the two substituents on the amino nitrogen of the aminocarbonyl taken together with the nitrogen atom form a nitrogen containing heterocyclic ring; cyano, halogen and nitro;

$R^8$ represents hydrogen, lower alkoxy, hydroxy, lower alkyl, lower alkylcarbonyloxy, lower alkoxycarbonyl, aminocarbonyl, lower alkylaminocarbonyl, di-lower alkylaminocarbonyl, amino, lower alkylamino, di-lower alkylamino, halogen, cyano or nitro;

$R^9$ represents a substituent selected from the group consisting of optionally substituted cycloalkyl, optionally substituted aryl, optionally substituted heteroaryl, and optionally substituted heteroarylalkyl wherein alkyl is unsubstituted or substituted with hydroxy, lower alkyl, halo-lower alkyl, lower alkoxy, amino, lower alkylamino and di-lower alkylamino, lower alkyl-carbonyloxy, aminocarbonyloxy, lower alkylaminocarbonyloxy, di-lower alkylaminocarbonyloxy or halogen;

$R^{10}$ represents a substituent selected from the group consisting of optionally substituted cycloalkyl, optionally substituted aryl, optionally substituted heteroaryl, and optionally substituted heteroarylalkyl;

$R^{11}$ represents lower alkyl, halo-lower alkyl, lower alkoxy-lower alkyl, aryl or aryl-lower alkyl;

or pharmaceutically acceptable salts thereof.

5. Compounds of formula (I) according to claim 2, wherein A is CH;

$R^1$ represents C(=O)$R^9$, S(=O)$_2R^{10}$, P(=O)(O$R^{11}$)$_2$, optionally substituted phenyl or optionally substituted heteroaryl;

$R^2$ represents hydrogen;

$R^3$ represents hydrogen, lower alkyl, halo-lower alkyl, lower alkoxy-lower alkyl, halo-lower alkoxy-lower alkyl, cycloalkyl, lower alkoxy, halo-lower alkoxy, lower alkoxy-lower alkoxy, alkenyloxy, cyano, halogen or nitro;

$R^4$ and $R^5$ represent hydrogen;

$R^6$ represents hydrogen, lower alkylcarbonyl or lower alkoxycarbonyl;

$R^7$ represents hydrogen, lower alkyl, halo-lower alkyl, optionally substituted heteroaryl, lower alkoxy, halo-lower alkoxy, lower alkoxy-lower alkoxy, alkenyloxy, lower alkylamino, di-lower alkylamino, lower alkylcarbonylamino, lower alkylcarbonyl, carboxy, lower alkoxycarbonyl, lower alkoxy-lower alkoxycarbonyl, cyano, halogen, or nitro;

$R^8$ represents a substituent selected from the group consisting of —O$R^{13}$ and $R^{13}$ represents alkyl, cycloalkyl-lower alkyl, halo-lower alkyl, hydroxy-lower alkyl, lower alkoxy-lower alkyl, acyloxy-lower alkyl, lower alkoxy-lower alkoxy-lower alkyl, halo-lower alkoxy-lower alkyl, carboxyalkyl, lower alkoxycarbonyl-lower alkyl; aminocarbonyl-lower alkyl wherein amino is unsubstituted or mono or di-substituted with lower alkyl, hydroxy-lower alkyl, alkoxy-lower alkyl, amino-lower alkyl, or wherein the two substituents on the amino nitrogen of the aminocarbonyl-lower alkyl taken together with the nitrogen atom form a nitrogen containing heterocyclic ring; amino-lower alkyl, wherein amino is unsubstituted or mono or di-substituted with lower alkyl, cycloalkyl-lower alkyl, hydroxy-lower alkyl, lower alkoxy-lower alkyl, or wherein the two substituents on the amino nitrogen of the aminoalkyl taken together with the nitrogen atom form a nitrogen containing heterocyclic ring; optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, lower alkoxycarbonyl, lower alkoxy-lower alkoxycarbonyl, lower alkylsulfonyl, lower alkoxy-lower alkylsulfonyl, di-lower alkylphosphonyl, and di-phenylphosphonyl;

$R^9$ represents a substituent selected from the group consisting of cycloalkyl, optionally substituted aryl, optionally substituted heteroaryl, heteroarylalkyl, a group —C(=O)—$R^{12}$, a group —C(=NOH)—$R^{12}$ and a group —C(=NO-alkyl)-$R^{12}$;

$R^{10}$ represents cycloalkyl, optionally substituted aryl, optionally substituted heteroaryl and heteroarylalkyl;

$R^{11}$ represents lower alkyl, halo-lower alkyl, lower alkoxy-lower alkyl, aryl or aryl-lower alkyl;

$R^{12}$ represents optionally substituted aryl or optionally substituted heteroaryl;

or pharmaceutically acceptable salts thereof.

6. Compounds of formula (I) according to claim 1, wherein A is CH;

$R^1$ represents C(=O)$R^9$, S(=O)$_2R^{10}$, optionally substituted phenyl or optionally substituted heteroaryl;

$R^2$ represents hydrogen;

$R^3$ represents hydrogen, lower alkyl, halo-lower alkyl, lower alkoxy-lower alkyl, halo-lower alkoxy-lower alkyl, cycloalkyl, lower alkoxy, halo-lower alkoxy, hydroxy, cyano, halogen or nitro;

$R^4$ and $R^5$ represent hydrogen;

$R^6$ represents hydrogen or methyl;

$R^7$ represents hydrogen, lower alkyl, halo-lower alkyl, lower alkoxy, halo-lower alkoxy, lower alkylamino, di-lower alkylamino, lower alkylcarbonylamino, lower alkylcarbonyl, carboxy, hydroxy, amino, cyano, halogen or nitro;

$R^8$ represents lower alkoxy, hydroxy, lower alkyl, lower alkylcarbonyloxy, lower alkoxycarbonyl, halogen, cyano or nitro;

$R^9$ represents a substituent selected from the group consisting of optionally substituted cycloalkyl, optionally substituted aryl, optionally substituted heteroaryl, and optionally substituted heteroarylalkyl wherein alkyl is unsubstituted or substituted by hydroxy, lower alkyl, halo-lower haloalkyl, lower alkoxy, amino, lower alkylamino, di-lower alkylamino, lower alkyl-carbonyloxy, aminocarbonyloxy, lower alkylaminocarbonyloxy, di-lower alkylaminocarbonyloxy or halogen;

$R^{10}$ represents a substituent selected from the group consisting of optionally substituted cycloalkyl, optionally substituted aryl, optionally substituted heteroaryl, and optionally substituted heteroarylalkyl;

or pharmaceutically acceptable salts thereof.

7. Compounds of formula (I) according to claim 2, wherein A is CH;

$R^1$ represents C(=O)$R^9$, S(=O)$^2R^{10}$, P(=O)(O$R^{11}$)$_2$, optionally substituted phenyl or optionally substituted heteroaryl;

$R^2$ represents hydrogen;

$R^3$ represents hydrogen, lower alkyl, halo-lower alkyl, lower alkoxy, cyano, halogen or nitro;

$R^4$ and $R^5$ represent hydrogen;

$R^6$ represents hydrogen;

$R^7$ represents hydrogen, lower alkyl, halo-lower alkyl, lower alkoxy, halo-lower alkoxy, lower alkoxy-lower alkoxy, alkenyloxy, lower alkylamino, di-lower alkylamino, lower alkylcarbonylamino, lower alkylcarbonyl, carboxy, lower alkoxycarbonyl, lower alkoxy-lower alkoxycarbonyl, cyano, halogen, or nitro;

$R^8$ represents —O$R^{13}$ and $R^{13}$ represents a substituent selected from the group consisting of alkyl, hydroxy-lower alkyl, lower alkoxy-lower alkyl, acyloxy-lower alkyl, lower alkoxy-lower alkoxy-lower alkyl, halo-lower alkoxy-lower alkyl, carboxyalkyl, lower alkoxycarbonyl-lower alkyl; amino-lower alkyl, wherein amino is unsubstituted or mono or di-substituted with lower alkyl, cycloalkyl-lower alkyl, hydroxy-lower alkyl, lower alkoxy-lower alkyl, or wherein the two substituents on the amino nitrogen of the amino-lower alkyl taken together with the nitrogen atom form a nitrogen containing heterocyclic ring; optionally substituted phenyl-lower alkyl, optionally substituted heteroaryl-lower alkyl, optionally substituted alkenyl, optionally substituted alkinyl, cycloalkyl, lower alkoxycarbonyl, lower alkoxy-lower alkoxycarbonyl, lower alkylsulfonyl, lower alkoxy-lower alkylsulfonyl, and di-lower alkylphosphonyl;

$R^9$ represents a substituent selected from the group consisting of cycloalkyl, optionally substituted aryl, optionally substituted heteroaryl, heteroarylalkyl, and a group —C(=NO-alkyl)-$R^{12}$;

$R^{10}$ represents cycloalkyl, optionally substituted aryl, optionally substituted heteroaryl, and heteroarylalkyl;

$R^{11}$ represents lower alkyl, halo-lower alkyl, lower alkoxy-lower alkyl, aryl or aryl-lower alkyl;

$R^{12}$ represents optionally substituted aryl or optionally substituted heteroaryl;

or pharmaceutically acceptable salts thereof.

8. Compounds of formula (I) according to claim 1, wherein A is CH;

$R^1$ represents C(=O)$R^9$, S(=O)$_2R^{10}$, optionally substituted phenyl or optionally substituted heteroaryl;

$R^2$ represents hydrogen;

$R^3$ represents hydrogen, lower alkyl, halo-lower alkyl, lower alkoxy, cyano or halogen;

$R^4$ and $R^5$ represent hydrogen;

$R^6$ represents hydrogen;

$R^7$ represents hydrogen, lower alkyl, halo-lower alkyl, lower alkoxy, halo-lower alkoxy, lower alkylamino, di-lower alkylamino, lower alkylcarbonylamino, lower alkylcarbonyl, cyano or halogen;

$R^8$ represents lower alkoxy, hydroxy, lower alkyl, lower alkylcarbonyloxy, halogen or cyano;

$R^9$ represents a substituent selected from the group consisting of cycloalkyl, optionally substituted aryl, optionally substituted heteroaryl, and optionally substituted heteroarylalkyl wherein alkyl is unsubstituted or substituted by hydroxy, lower alkyl, lower alkoxy or amino;

$R^{10}$ represents optionally substituted aryl, optionally substituted heteroaryl, or heteroarylalkyl;

or pharmaceutically acceptable salts thereof.

9. Compounds of formula (I) according to claim 2, wherein A is CH;

$R^1$ represents C(=O)$R^9$ or optionally substituted heteroaryl;

$R^2$ represents hydrogen;

$R^3$ represents hydrogen, lower alkyl, halo-lower alkyl, lower alkoxy, cyano or halogen;

$R^4$ and $R^5$ represent hydrogen;

$R^6$ represents hydrogen;

$R^7$ represents hydrogen, lower alkyl, halo-lower alkyl, lower alkoxy, lower alkylcarbonylamino, lower alkylcarbonyl, carboxy, lower alkoxycarbonyl, lower alkoxy-lower alkoxycarbonyl, cyano or halogen;

$R^8$ represents —O$R^{13}$ and $R^{13}$ represents a substituent selected from the group consisting of alkyl, hydroxy-lower alkyl, lower alkoxy-lower alkyl, acyloxy-lower alkyl, lower alkoxy-lower alkoxy-lower alkyl, carboxyalkyl, lower alkoxycarbonyl-lower alkyl; amino-lower alkyl, wherein amino is unsubstituted or mono or di-substituted with lower alkyl, cycloalkyl-lower alkyl, hydroxy-lower alkyl, lower alkoxy-lower alkyl, or wherein the two substituents on the amino nitrogen of the amino-lower alkyl taken together with the nitrogen atom form a nitrogen containing heterocyclic ring; optionally substituted alkenyl, optionally substituted alkinyl, cycloalkyl, lower alkoxycarbonyl, lower alkoxy-lower alkoxycarbonyl, lower alkylsulfonyl, lower alkoxy-lower alkylsulfonyl, and di-lower alkylphosphonyl;

$R^9$ represents cycloalkyl, optionally substituted aryl, optionally substituted heteroaryl, heteroarylalkyl, and —C(=NO-alkyl)-$R^{12}$;

$R^{12}$ represents optionally substituted aryl or optionally substituted heteroaryl;

or pharmaceutically acceptable salts thereof.

10. Compounds of formula (I) according to claim 1, wherein A is CH;

$R^1$ represents C(=O)$R^9$ or optionally substituted heteroaryl;

$R^2$ represents hydrogen;

$R^3$ represents hydrogen, lower alkyl, halo-lower alkyl, lower alkoxy, cyano or halogen;

$R^4$ and $R^5$ represent hydrogen;

$R^6$ represents hydrogen;

$R^7$ represents hydrogen, lower alkyl, halo-lower alkyl, lower alkoxy, lower alkylcarbonylamino, cyano or halogen;

$R^8$ represents lower alkoxy, hydroxy, lower alkyl, lower alkylcarbonyloxy, halogen or cyano;

$R^9$ represents a substituent selected from the group consisting of cycloalkyl, optionally substituted aryl, optionally substituted heteroaryl, and optionally substituted heteroarylmethyl wherein the methylene group is unsubstituted or substituted by hydroxy, lower alkyl or lower alkoxy;

or pharmaceutically acceptable salts thereof.

11. The compounds of claim 2, wherein A is CH;

$R^1$ represents C(=O)$R^9$;

$R^2$ represents hydrogen;

$R^3$ represents hydrogen or lower alkyl;

$R^4$ and $R^5$ represent hydrogen;

$R^6$ represents hydrogen;

$R^7$ represents hydrogen or lower alkoxy;

$R^8$ represents —O$R^{13}$ and $R^{13}$ represents lower alkyl, benzyl or allyl;

$R^9$ represents optionally substituted aryl or optionally substituted heteroaryl;

or pharmaceutically acceptable salts thereof.

12. The compounds of claim 2,
wherein A is CH;

$R^1$ represents C(=O)$R^9$;

$R^2$, $R^3$, $R^4$, $R^5$, $R^6$ and $R^7$ represent hydrogen;

$R^8$ represents lower alkoxy;

$R^9$ represents optionally substituted aryl or optionally substituted heteroaryl;

or pharmaceutically acceptable salts thereof.

13. The compounds selected from the group consisting of
3-(m-benzoylaminophenyl)-5-(p-methoxyphenylamino) pyridine,
3-(m-[2-chloro-3-pyridylcarbonyl]aminophenyl)-5-(p-methoxyphenylamino)pyridine,
5-(p-methoxyphenylamino)-3-(m-[2-pyridazinylcarbonyl]aminophenyl)pyridine,
3-(m-[2-furoyl]aminophenyl)-5-(p-methoxyphenylamino)pyridine,
5-(p-methoxyphenylamino)-3-(m-[4-pyridylcarbonyl] aminophenyl)pyridine,
5-(p-methoxyphenylamino)-3-(m-[2-pyridylcarbonyl] aminophenyl)pyridine,
3-(m-[2-chlorobenzoyl]aminophenyl)-5-(p-methoxyphenylamino)pyridine,
5-(p-methoxyphenylamino)-3-(m-[2-thiophenylcarbonyl] aminophenyl)pyridine,
3-(m-[2-ethoxybenzoyl]aminophenyl)-5-(p-methoxyphenylamino)pyridine,
5-(p-Methoxyphenylamino)-3-(m-[2-pyridylamino]phenyl)pyridine
and pharmaceutically acceptable salts thereof.

14. A pharmaceutical composition comprising a compound of formula (I) according to claim 2 and a pharmaceutically acceptable carrier.

15. The compound of claim 2, wherein said compound has the formula:

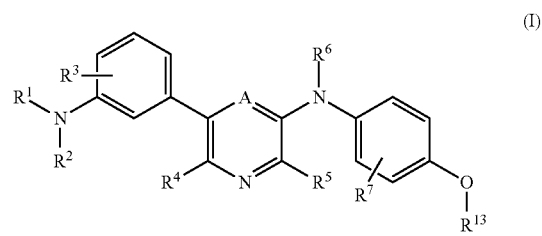

wherein A is CH, or C-lower alkyl; $R^{13}$ is lower alkyl, cycloalkyl-lower alkyl, halo-lower alkyl, hydroxy-lower alkyl, lower alkoxy-lower alkyl, acyloxy-lower alkyl, lower alkoxy-lower alkoxy-lower alkyl, halo-lower alkoxy-lower alkyl, carboxyalkyl, or lower alkoxycarbonyl-lower alkyl or pharmaceutically acceptable salts thereof.

16. The compound of claim 15 wherein $R^1$ is C(=O)$R^9$, $R^9$ is optionally substituted aryl, $R^2$, $R^3$, $R^4$, $R^5$, $R^6$ and $R^7$ are hydrogen.

17. The compound of claim 1 wherein $R^7$ represents one substituent.

18. The compound of claim 11 having the formula

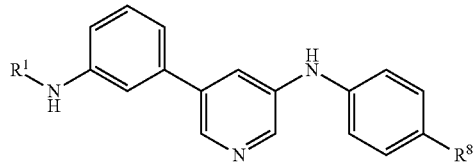

wherein
$R^1$ is $C_6H_5$—CO— or

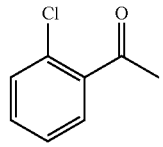

and $R^8$ is lower alkoxy or a pharmaceutically acceptable salts thereof.

19. A compound of claim 11 having the formula

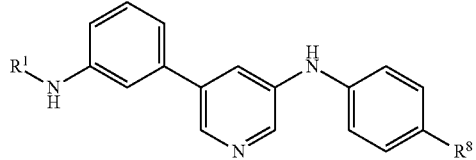

wherein
$R^1$ is a group of formula

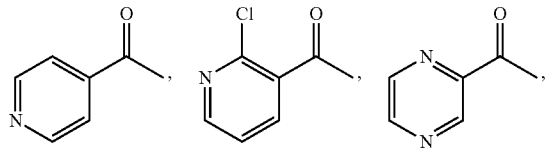

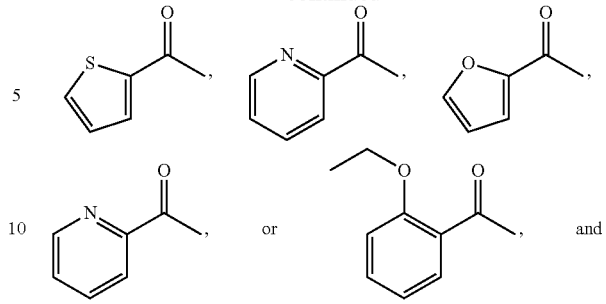

$R^8$ is lower alkoxy or a pharmaceutically acceptable salts thereof.

20. The compound of claim 15 wherein A is —CH—.

21. The compound of claim 20 wherein said compound is 3-(m-[2-chlorobenzoyl]aminophenyl)-5-(p-methoxyphenylamino)pyridine or pharmaceutically acceptable salts thereof.

* * * * *